US011604145B2

(12) United States Patent
Gabibov et al.

(10) Patent No.: US 11,604,145 B2
(45) Date of Patent: Mar. 14, 2023

(54) METHOD FOR ULTRA-HIGH PERFORMANCE SCREENING OF BIOLOGICAL OBJECTS

(71) Applicant: SHEMYAKIN-OVCHINNIKOV INSTITUTE OF BIOORGANIC CHEMISTRY OF THE RUSSIAN ACADEMY OF SCIENCES, Moscow (RU)

(72) Inventors: Alexander Gabibovich Gabibov, Moscow (RU); Ivan Vitalievich Smirnov, Moscow (RU); Stanislav Sergeevich Terekhov, Yoshkar-Ola (RU)

(73) Assignee: SHEMYAKIN-OVCHINNIKOV INSTITUTE OF BIOORGANIC CHEMISTRY OF THE RUSSIAN ACADEMY OF SCIENCES, Moscow (RU)

( * ) Notice: Subject to any disclaimer, the term of this patent is extended or adjusted under 35 U.S.C. 154(b) by 560 days.

(21) Appl. No.: 16/496,595

(22) PCT Filed: Mar. 13, 2018

(86) PCT No.: PCT/RU2018/000155
§ 371 (c)(1),
(2) Date: Sep. 23, 2019

(87) PCT Pub. No.: WO2018/174748
PCT Pub. Date: Sep. 27, 2018

(65) Prior Publication Data
US 2020/0256801 A1    Aug. 13, 2020

(30) Foreign Application Priority Data
Mar. 24, 2017  (RU) .................... 2017109892

(51) Int. Cl.
*G01N 21/76*   (2006.01)
*C12Q 1/02*    (2006.01)
*C12Q 1/46*    (2006.01)
*C12Q 1/6869*  (2018.01)

(52) U.S. Cl.
CPC ............. *G01N 21/76* (2013.01); *C12Q 1/025* (2013.01); *C12Q 1/46* (2013.01); *C12Q 1/6869* (2013.01)

(58) Field of Classification Search
CPC .......... G01N 21/76; G01N 2015/1006; G01N 2015/1481; G01N 15/1459; G01N 15/1484; G01N 33/48; C12Q 1/025; C12Q 1/46; C12Q 1/6869; C12Q 1/02; B01F 23/40
See application file for complete search history.

(56) References Cited

U.S. PATENT DOCUMENTS

| 7,384,778 B2 * | 6/2008 | Chen ................. C12Q 1/18 435/287.1 |
| 9,513,207 B2 | 12/2016 | Smith et al. |
| 10,920,294 B2 * | 2/2021 | Kohsaka ............... C22C 38/00 |
| 2014/0179544 A1 | 6/2014 | Steenblock et al. |
| 2015/0247182 A1 * | 9/2015 | Faham ................ C12Q 1/6844 506/4 |

FOREIGN PATENT DOCUMENTS

| JP | 7-313858 A | 12/1995 |
| WO | WO 2015/103190 A1 | 7/2015 |

OTHER PUBLICATIONS

Chan et al, High-throughput screening of microchip-synthesized genes in programmable double emulsion droplets, 2017, Nanoscale, 9, 3485-3495 (Year: 2017).*
Teh et al, Microfluidic Double Emulsions for the Formation of Lipid Vesicles and the Controlled Encapsulation of Cells, 2009, Thirteenth International Conference on Miniaturized Systems for Chemistry and Life Sciences (Year: 2009).*
Wu et al, A double-emulsion microfluidic platform for in vitro green fluorescent protein expression, 2011, J. Micromech. Microeng., 21, 054032 (7pp) (Year: 2011).*
Zhang et al, A programmable microenvironment for cellular studies via microfluidic-generated double emulsions, 2013, Biomaterials, 34, 4564-4572. (Year: 2013).*
Terekhov et al, Microfluidic droplet platform for ultrahigh-throughput single-cell screening of biodiversity, 2017, PNAS, 114, 1550-2555. (Year: 2017).*
Marcy et al, Dissecting biological "dark matter" with single-cell genetic analysis of rare and uncultivated TM7 microbes from the human mouth, PNAS, 104, 11889-11894 (Year: 2007).*
Chan, Microfluidics-generated Double Emulsion Platform for High-Throughput Screening and Multicellular Spheroid Production with Controllable Microenvironment, Thesis, publicly available in 2015, pp. 1-138. (Year: 2015).*
Terekhov et al, Supplemental information, Microfluidic droplet platform for ultrahigh-throughput single-cell screening of biodiversity, 2017, PNAS, 114, 1550-2555, pp. 1-9. (Year: 2015).*
Slatko et al, Overview of Next Generation Sequencing Technologies, 2018, Curr Protoc Mol Biol., 122(1): e59, 15 pages (Year: 2018).*
Aharoni et al, High-Throughput Screening of Enzyme Libraries: Thiolactonases Evolved by Fluorescence-Activated Sorting of Single Cells in Emulsion Compartments, 2005, 12, pp. 1281-1289. (Year: 2005).*

(Continued)

*Primary Examiner* — Narayan K Bhat
(74) *Attorney, Agent, or Firm* — Oblon, McClelland, Maier & Neustadt, L.L.P.

(57) ABSTRACT

The invention relates to the field of biotechnology and pharmaceutics. Proposed is a method for ultra-high performance screening of biological objects which is based on microfluidic generation of droplets of a biocompatible water-in-oil-in-water double emulsion, and also a method for producing a monodisperse biocompatible water-in-oil-in-water double emulsion. The invention can be used in diagnosing conditions and diseases in mammals, as well as for investigating biological objects.

20 Claims, 23 Drawing Sheets

Specification includes a Sequence Listing.

(56) References Cited

OTHER PUBLICATIONS

Kim et al, Development of W /O/W Multiple Emulsion Formulation Containing Burkholderia gladioli, 2005, J. Microbial. Biotechnol., 15, 29-34. (Year: 2005).*
Zhou, Y., et al., "High-throughput screening of a CRISPR/Cas9 library for functional genomics in human cells", Nature, Research Letter, vol. 000, 2014, pp. 1-5.
Bleicher, K. H., et al., "Hit and Lead Generation: Beyond High-Throughput Screening", Nature Reviews, vol. 2, May 2003, pp. 369-378.
Zheng, F., et al., "A highly efficient cocaine-detoxifying enzyme obtained by computational design", Nature Communications, 2014, pp. 1-8.
Arnold, F.H., "Combinatonal and computational challenges for biocatalyst design", Nature, vol. 409, Jan. 11, 2001, pp. 253-257.
Bajorath, J., "Integration of Virtual and High-Throughput Screening", Nature, vol. 1, Nov. 2002, pp. 882-894.
Inglese, J., et al., "Reporting data from high-throughput screening of small-molecule libraries", Nature Chemical Biology, vol. 3 No. 8, Aug. 2007, pp. 438-441.
Sackmann, E.K., et al., "The present and future role of microfluidics in biomedical research", Nature, vol. 507, Mar. 13, 2014, pp. 181-189.
Agresti, J. J., et al., "Ultrahigh-throughput screening in drop-based microfluidics for directed evolution", PNAS, vol. 107, Mar. 2, 2010, pp. 4004-4009.
Kintses, B., et al., "Picoliter Cell Lysate Assays in Microfluidic Droplet Compartments for Directed Enzyme Evolution", Chemistry & Biology, vol. 19, Aug. 24, 2012, pp. 1001-1009.
Fallah-Araghi, A., et al., "A completely in vitro ultrahigh-throughput droplet-based microfluidic screening system for protein engineering and directed evolution", The Royal Society of Chemistry, Lab Chip, 2012, vol. 12, pp. 882-891 (with cover page).
Mazutis, L., et al., "Single-cell analysis and sorting using droplet-based microfluidics", Nat. Protoc., vol. 8 No. 5, May 2013, pp. 870-891.
Macosko, E.Z., et al., "Highly Parallel Genome-wide Expression Profiling of Individual Cells Using Nanoliter Droplets", Cell, vol. 161, May 21, 2015, pp. 1202-1214 (with cover page).
Colin, P.-Y., et al., "Ultrahigh-throughput discovery of promiscuous enzymes by picodroplet functional metagenomics", Nature Communications, 2015, pp. 1-12.
Lam, K. S., et al., "A new type of synthetic peptide library for identifying ligand-binding activity", Letters to Nature, vol. 354, Nov. 7, 1991, pp. 82-84.
Zahnd, C., et al., "Ribosome display: selecting and evolving proteins in vitro that specifically bind to a target", Nature Methods, vol. 4 No. 3, Mar. 2007, pp. 269-279.
De Bruin, R., et al., "Selection of high-affinity phage antibodies from phage display libraries", Nature Biotechnology, vol. 17, Apr. 1999, pp. 397-399.
Lee, C. M. Y., et al., "Selection of human antiobody fragments by phage display", Nature Protocols, vol. 2 No. 11, 2007, pp. 3001-3008.
Rockberg, J., et al., "Epitope mapping of antibodies using bacterial surface display", Nature Methods, vol. 5 No. 12, Dec. 2008, pp. 1039-1045.
Boder, E.T., et al., "Yeast surface display for screening combinatorial polypeptide libraries", Nature Biotechnology, vol. 15, Jun. 1997, pp. 553-557.
Li, C. -Z., et al., "Identification of HBsAg-specific antibodies from a mammalian cell displayed full-length human antibody library of healthy immunized donor", Cellular & Molecular Immunology, vol. 9, 2012, pp. 184-190.
Tuerk. C., et al., "Systematic Evolution of Ligands by Exponential Enrichment;; RNA Ligands to Bacteriophage T4 DNA Polymerase", Science, Research Articles, vol. 249, Aug. 3, 1990, pp. 505-510 (with cover page).
Seelig, B., "mRNA display for the selection and evolution of enzymes from in vitro-translated protein libraries", Nature Protocols, vol. 6 No. 4, 2011, pp. 540-552.
Chen, I., et al., "A general strategy for the evolution of bond-forming enzymes using yeast display", PNAS, vol. 108 No. 28, Jul. 12, 2011, pp. 11399-11404.
"A New Tack on Herbicide Resistance", Science, vol. 304, May 21, 2004, p. 1089.
Tsai. P. -C., et al., "Enzymes for the Homeland Defense: Optimizing Phosphotriesterase for ths Hydrolysis of Organophosphate Nerve Agents", Biochemistry, vol. 51, 2012, pp. 6463-6475.
Esvelt, K.M., et al., "A system for the continuous directed evolution of biomolecules", Nature, vol. 472, Apr. 28. 2011, pp. 499-503 (with cover pages).
Yoo, T.H., et al., "Directed Evolution of Highly Selective Proteases Using a Novel FACS Based Screen that Capitalizes on the p53 Regulator MDM2", Chembiochem., vol. 13 No. 5, Mar. 19, 2012, 10 pages.
Chen, C.P., et al., "Ecstasy, an adjustable membrane-tethered/soluble protein expression system for the directed evolution of mammalian proteins", Protein Engineering, Design & Selection, vol. 25 No. 7, 2012, pp. 367-375.
Bernath, K., et al., "In vitro compartmentalization by double emulsions: sorting and gene enrichment by fluorescence activated cell sorting", Analytical Biochemistry, vol. 325, 2004, pp. 151-157.
Miller, O.J., et al., "Directed evolution by in vitro compartmentalization", Nature Methods, vol. 3 No. 7, Jul. 2006, pp. 561-570.
Mark, D., et al., "Microfluidic lab-on-a-chip platforms: requirements, characteristics and applications", Chemical Society Reviews, vol. 39, 2010, pp. 1153-1182 (with cover page).
Ghadessy, F.J., et al., "A novel emulsion mixture for in vitro compartmentalization of transcription and translation in the rabbit reticulocyte system", Protein Engineering, Design & Selection, vol. 17 No. 3, 2004, pp. 201-204.
Gruner, P., et al., "Stabilisers for water-in-fluorinated-oil dispersions: Key properties for microfluldic applications", Current Opinion in Colloid & Interface Science, vol. 20, 2015, pp. 183-191.
Holtze, C., et al., "Biocompatible surfactants for water-in-fluorocarbon emulsions", The Royal Society of Chemistry, Lab Chip, vol. 8, 2008, pp. 1632-1639 (with cover page).
Clausell-Tormos, J., et al., "Droplet-Based Microfluidic Platforms for the Encapsulation and Screening of Mammalian Cells and Multicellular Organisms", Chemistry & Biology, vol. 15, May 2008, pp. 427-437.
Ahn, K., et al., "Dielectrophoretic manipulation of drops for high-speed microfluidic sorting devices", Applied Physics Letters, vol. 8, 2006, pp. 024104-1-024104-3 (with cover page).
Baret, J. -C., et al., "Fluorescence-activated droplet sorting (FADS). efficient microfluidic cell sorting based on enzymatic activity", The Royal Society of Chemistry, Lab on a Chip, vol. 9 No. 13, Jul. 7, 2009, pp. 1817-1972.
Romanowsky, M.B., et al., "High throughput production of single core double emulsions in a parallelized microfluidic device", Lab on a Chip, vol. 12, 2012, pp. 802-807.
Yan, J., et al., "Monodisperse Water-in-Oil-in-Water (W/O/W) Double Emulsion Droplets as Uniform Compartments for High-Throughput Analysis via Flow Cytometry", Micromachines, vol. 4, 2013, pp. 402-413.
Terekhove, S.S., "Methods tor ultrahigh performance screening of cell libraries using microfluidic technologies for identification of biocatalytic and antimicrobial activity", Moscow State University, Chemistry Department, 2016, pp. 1-163 (with partial English translation).
Belousov, et al., Micro- and nanotechnologies for biological and medical research. Parts, Drop microfluidic technologies, University ITMO, St. Petersburg, 2015, pp. 4-56 (with cover pages, with English abstract).
Russian Search Report and Written Opinion dated Sep. 29, 2017 in Russian Patent Application No. 2017109892 (with English translation of written opinion only), citing documents AA, AB, AE, AF, BC, BD and BF therein, 11 pages.

(56) References Cited

OTHER PUBLICATIONS

Supplemental Written Opinion dated Feb. 1, 2018 in Russian Patent Application No. 2017109892 (with English translation), 8 pages.

* cited by examiner

A

10 h growth

| Fraction | 1 | 2 | 3 | 4 | 5 | 6 | 7 | 0 | Avg |
|---|---|---|---|---|---|---|---|---|---|
| 1 | 22 | 154 | 73 | 234 | 243 | 49 | 55 | 265 | 137 |
| 2 | 148 | 403 | 193 | 244 | 240 | 118 | 125 | 400 | 234 |
| 3 | 69 | 171 | 377 | 775 | 831 | 126 | 179 | 937 | 433 |
| 4 | 225 | 254 | 766 | 260 | 365 | 81 | 97 | 203 | 281 |
| 5 | 259 | 255 | 784 | 320 | 295 | 77 | 71 | 332 | 299 |
| 6 | 55 | 121 | 136 | 86 | 71 | 78 | 76 | 147 | 96 |
| 7 | 60 | 117 | 159 | 107 | 73 | 56 | 244 | 816 | 204 |
| 0 | 263 | 384 | 1006 | 225 | 348 | 149 | 833 | 1160 | 546 |
| Avg | 138 | 232 | 437 | 281 | 308 | 92 | 210 | 533 | 279 |

72 h growth

| Fraction | 1 | 2 | 3 | 4 | 5 | 6 | 7 | 0 | Avg |
|---|---|---|---|---|---|---|---|---|---|
| 1 | 602 | 417 | 1268 | 123 | 116 | 50 | 1496 | 1640 | 714 |
| 2 | 445 | 372 | 1373 | 1005 | 312 | 180 | 2902 | 2361 | 1119 |
| 3 | 1308 | 1547 | 1219 | 1963 | 1637 | 218 | 2737 | 2326 | 1619 |
| 4 | 144 | 912 | 2199 | 2041 | 2156 | 165 | 3466 | 1476 | 1570 |
| 5 | 108 | 350 | 1702 | 2014 | 2765 | 114 | 2817 | 2655 | 1565 |
| 6 | 49 | 180 | 200 | 113 | 113 | 129 | 207 | 555 | 193 |
| 7 | 1568 | 2956 | 3069 | 3686 | 2851 | 176 | 3711 | 3821 | 2730 |
| 0 | 1538 | 2698 | 2684 | 1685 | 2867 | 564 | 3849 | 3721 | 2451 |
| Avg | 720 | 1179 | 1714 | 1579 | 1602 | 199 | 2648 | 2319 | 1495 |

Fig. 30.

METHOD FOR ULTRA-HIGH PERFORMANCE SCREENING OF BIOLOGICAL OBJECTS

BACKGROUND OF THE INVENTION

Field of the Invention

The invention relates to the field of biotechnology and pharmaceuticals.

Description of the Related Art

Modern biotechnology and pharmaceuticals are extremely high-tech areas, whose success is closely related to the development of new principles for the screening of various types of biological activity. The opportunities that the "post-genomic" era opens up allow us to identify new targets for the search for therapeutic agents, Zhou Y., Zhu S., Cai C., Yuan P., Li C., et al. High-throughput screening of a CRISPR/Cas9 library for functional genomics in human cells. //Nature.—2014.—Vol. 509, No 7501.—P. 487-491, as well as to carry out a virtual screening of potential drug candidates in silico; Bleicher K. H., Bohm H.-J., Muller K., Alanine A. I. Hit and lead generation: beyond high-throughput screening. //Nat Rev Drug Discov.—2003.—Vol. 2, No 5.—P. 369-378.

Despite the enormous prospects for molecular modeling methods, this approach is not universal, since the resources of currently existing supercomputers do not allow one to calculate interactions of biomolecules de novo. Moreover, they are based on various approximations that require the crystal structure of the target, its dynamics, as well as a clear understanding of the mechanism of interaction. See Zheng F., Xue L., Hou S., Liu J., Zhan M., et al. A highly efficient cocaine-detoxifying enzyme obtained by computational design. //Nat Commun.—2014.—Vol. 5.—P. 3457. Combinatorial screening approaches are based on experiment, on the contrary, do not require any additional data for screening of the new biological activity. They are based on the assumption that a sufficiently large sample of variable functionalities already contains the desired activity due to its diversity. Hence, the task of the researcher is only in its efficient selection from the initial pool. See Arnold F. H. Combinatorial and computational challenges for biocatalyst design. //Nature.—2001.—Vol. 409, No 6817.—P. 253-257.

Despite the unique ability for screening of biological activity in silico de novo, the vast majority of modern drugs were developed by using a combination of computer modeling methods and high-throughput screening of drug candidates. See Bajorath J. Integration of virtual and high-throughput screening. //Nat Rev Drug Discov.—2002.—Vol. 1, No 11.—P. 882-894. Currently, high-throughput screening is based on automated robotic stations, however there is an obvious tendency for the biotechnological platforms to switch to the lab-on-a-chip format based on modern advances in microfluidics. See Inglese J., Shamu C. E., Guy R. K. Reporting data from high-throughput screening of small-molecule libraries. //Nat Chem Biol.—2007.—Vol. 3, No 8.—P. 438-441; and Sackmann E. K., Fulton A. L., Beebe D. J. The present and future role of microfluidics in biomedical research. //Nature.—2014.—Vol. 507, No 7491.—P. 181-189. The use of microfluidics leads to the miniaturization of equipment, reducing the cost of reagents and operation. There is a multiple increase in productivity resulted from the transition to the ultrahigh-throughput screening based on microfluidic droplet technologies. See Agresti J. J., Antipov E., Abate A. R., Ahn K., Rowat A. C., et al. Ultrahigh-throughput screening in drop-based microfluidics for directed evolution. //Proceedings of the National Academy of Sciences.—2010.—Vol. 107, No 9.—P. 4004-4009. Despite the significant successes, there are still a sufficient number of unsolved problems in terms of the technology of microfluidic flow formation, selection systems and identification of biochemical and biological activity on a single cell level. See Agresti et al.; Kintses B., Hein C., Mohamed Mark F., Fischlechner M., Courtois F., et al. Picoliter Cell Lysate Assays in Microfluidic Droplet Compartments for Directed Enzyme Evolution. //Chemistry & Biology.—2012.—Vol. 19, No 8.—P. 1001-1009; Fallah-Araghi A., Baret J.-C., Ryckelynck M., Griffiths A. D. A completely in vitro ultrahigh-throughput droplet-based microfluidic screening system for protein engineering and directed evolution. //Lab on a Chip.—2012.—Vol. 12, No 5.—P. 882-891; Mazutis L., Gilbert J., Ung W. L., Weitz D. A., Griffiths A. D., et al. Single-cell analysis and sorting using droplet-based microfluidics. //Nat. Protocols.—2013.—Vol. 8, No 5.—P. 870-891; Macosko Evan Z., Basu A., Satija R., Nemesh J., Shekhar K., et al. Highly Parallel Genome-wide Expression Profiling of Individual Cells Using Nanoliter Droplets. //Cell.—2015.—Vol. 161, No 5.—P. 1202-1214; and Colin P.-Y., Kintses B., Gielen F., Miton C. M., Fischer G., et al. Ultrahigh-throughput discovery of promiscuous enzymes by picodroplet functional metagenomics. //Nat Commun.—2015.—Vol. 6.—P. 10008.

The invention relates to the creation of a universal ultra-high-throughput microfluidic platform for screening of various types of biocatalytic and biological activity of proteins and cells.

Currently, there are many different ultrahigh-throughput approaches that efficiently select different biomolecules with high specificity and high affinity of binding to the target molecules: screening using microspheres, ribosome display, phage display, bacterial display, yeast display, display on mammalian cells, SELEX. See Lam K. S., Salmon S. E., Hersh E. M., Hruby V. J., Kazmierski W. M., et al. A new type of synthetic peptide library for identifying ligand-binding activity. //Nature.—1991.—Vol. 354, No 6348.—P. 82-84; Zahnd C., Amstutz P., Pluckthun A. Ribosome display: selecting and evolving proteins in vitro that specifically bind to a target. //Nat Meth.—2007.—Vol. 4, No 3.—P. 269-279; Bruin R. d., Spelt K., Mol J., Koes R., QuattrocchioFrancesca. Selection of high-affinity phage antibodies from phage display libraries. //Nat Biotech.—1999.—Vol. 17, No 4.—P. 397-399; Lee C. M. Y., Iorno N., Sierro F., Christ D. Selection of human antibody fragments by phage display. //Nat. Protocols.—2007.—Vol. 2, No 11.—P. 3001-3008; Rockberg J., Lofblom J., Hjelm B., Uhlen M., Stahl S. Epitope mapping of antibodies using bacterial surface display. //Nat Meth.—2008.—Vol. 5, No 12.—P. 1039-1045; Boder E. T., Wittrup K. D. Yeast surface display for screening combinatorial polypeptide libraries. //Nat Biotech.—1997.—Vol. 15, No 6.—P. 553-557; Li C.-Z., Liang Z.-K., Chen Z.-R., Lou H.-B., Zhou Y., et al. Identification of HBsAg-specific antibodies from a mammalian cell displayed full-length human antibody library of healthy immunized donor. //Cell Mol Immunol.—2012.—Vol. 9, No 2.—P. 184-190; and Tuerk C., Gold L. Systematic evolution of ligands by exponential enrichment: RNA ligands to bacteriophage T4 DNA polymerase. //Science.—1990.—Vol. 249, No 4968.—P. 505-510. At the same time, the development of ultrahigh-throughput methods focused on isolation of chemical or biological activity, unrelated to binding, is not always a straightforward strategy. First of all, these methods are not universal and in each specific case have a number of serious drawbacks, which limit their application. In particular, many of them are applicable only for screening of activity associated with the formation of a covalent bond. See Seelig B. mRNA display for the selection and evolution of enzymes from in vitro-translated protein libraries. //Nat. Protocols.—2011.—Vol. 6, No 4.—P. 540-552; and Chen I., Dorr B. M., Liu D. R. A general strategy for the evolution of bond-forming enzymes using yeast display//Proceedings of the National Academy of Sciences.—2011.—Vol. 108, No 28.—P. 11399-11404. Others require the involvement of additional molecular mechanisms, such as the advantage of growth rate or the emergence of survival in the selection process. See Castle L. A., Siehl D. L., Gorton R., Patten P. A., Chen Y. H., et al. Discovery and Directed Evolution of a Glyphosate Tolerance Gene. //Science.—2004.—Vol. 304, No 5674.—P. 1151-1154; Tsai P.-C., Fox N., Bigley A. N., Harvey S. P., Barondeau D. P., et al. Enzymes for the Homeland Defense: Optimizing Phosphotriesterase for the Hydrolysis of Organophosphate Nerve Agents. //Biochemistry.—2012.—Vol. 51, No 32.—P. 6463-6475; and Esvelt K. M., Carlson J. C., Liu D. R. A system for the continuous directed evolution of biomolecules//Nature.—2011.—Vol. 472, NM 7344.—P. 499-503. Some methods use specific substrates that form fluorescent products anchored on the cell wall (or highly hydrophobic) as a result of a biochemical reaction catalyzed by an enzyme of interest, which allows the most active cells to be selected by fluorescence of the reaction product using fluorescence activated cell sorting (FACS). See Yoo T. H., Pogson M., Iverson B. L., Georgiou G. Directed Evolution of Highly Selective Proteases by Using a Novel FACS-Based Screen that Capitalizes on the p53 Regulator MDM2. //ChemBioChem.—2012.—Vol. 13, No 5.—P. 649-653; and Chen C.-P., Hsieh Y.-T., Prijovich Z. M., Chuang H.-Y., Chen K.-C., et al. ECSTASY, an adjustable membrane-tethered/soluble protein expression system for the directed evolution of mammalian proteins. //Protein Engineering Design and Selection.—2012.—Vol. 25, No 7.—P. 367-375.

Thus, to create a universal screening technology for selection of specific activity in microfluidic droplets, the solution of two fundamental tasks is required: 1. The detection of activity at the level of single droplets; 2. The isolation of single active droplets from the mixture.

The simplest solution of these problems was demonstrated in Bernath et al., firstly. See Bernath K., Hai M., Mastrobattista E., Griffiths A. D., Magdassi S., et al. In vitro compartmentalization by double emulsions: sorting and gene enrichment by fluorescence activated cell sorting. //Analytical Biochemistry.—2004.—Vol. 325, No 1.—P. 151-157. Fluorescence was used as an analytical signal for highly sensitive detection of biocatalytic activity, and emulsion droplets were selected using a standard cell sorter (FACS). In this case, the fundamental achievement was the transition from a single water-in-oil emulsion to a double water-in-oil-in-water emulsion. This allowed analyzing the individual biocatalytic activity of enzymes encoded by isolated genes.

Subsequent improvement of the emulsion screening technology is associated with the improvement of the compartments themselves—emulsion droplets. The fact is that the generation of both single and double emulsions was carried out using homogenizers. See Miller O. J., Bernath K., Agresti J. J., Amitai G., Kelly B. T., et al. Directed evolution by in vitro compartmentalization. //Nat Meth.—2006.—Vol. 3, No 7.—P. 561-570. Despite the fact that the use of homogenizers enable generate enormous number of droplets, this technology has several fundamental limitations:

stochastic generation of emulsion droplets leads to an extremely high polydispersity;

the resulting double emulsion is a multi-compartment (ie, one drop carries several isolated drops);

emulsion generation takes place under severe conditions of high shear stress unacceptable for most biological objects.

These drawbacks significantly reduce the sensitivity of this method. The droplets of different size and granularity have different volume and scattering. Consequently, this lead to different reaction conditions inside the droplets. In addition, this significantly reduce the maximum throughput (specifically, the proportion of drops of the target size and granularity is 1-5%) and prohibit encapsulation of various biological objects that are sensitive to emulsification (mammalian cells, many types of microorganisms, as well as multicellular organisms).

We provide the solution to these problems based on the application of microfluidic emulsification technologies. Advances in the field of microfluidics are based on the use of microfluidic chips, miniature devices consisting of channels and textures ranging in size from several tens to micrometers, which enable to implement to the concept of lab-on-a-chip. See Mark D., Haeberle S., Roth G., von Stetten F., Zengerle R. Microfluidic lab-on-a-chip platforms: requirements, characteristics and applications. //Chemical Society Reviews.—2010.—Vol. 39, No 3.—P. 1153-1182.

The encapsulation of living cells and microorganisms in individual droplets of a microfluidic emulsion is of great interest, since it opens up unique possibilities for studying the unique properties of individual objects among their population diversity. Advances in this area are associated with the development of inert organic liquids and biocompatible emulsifiers. The simplest solution to this problem is the use of mineral oil and highly efficient biocompatible polysiloxane-based emulsifiers (for example, cetyl polyethylene glycol/polypropylene glycol-10/1 dimethicone). See Miller et al.; and Ghadessy F. J., Holliger P. A novel emulsion mixture for in vitro compartmentalization of transcription and translation in the rabbit reticulocyte system. //Protein Engineering Design and Selection.—2004.—Vol. 17, No. 3.—P. 201-204. This approach was successfully applied for compartmentalization of living cells of facultative anaerobes (bacteria *Escherichia coli*, *Bacillus subtilis*, and yeast *Saccharomyces cerevisiae*), as well as for cell-free in vitro transcription/translation. At the same time, mineral oil severely restricts the transport of gases, which is a fundamental disadvantage that inhibits the growth of microorganisms and prohibit its application for encapsulation of mammalian cells and numerous types of aerobic bacteria. See Gruner P., Riechers B., Chacon Orellana L. A., Brosseau Q., Maes F., et al. Stabilisers for water-in-fluorinated-oil dispersions: Key properties for microfluidic applications. //Current Opinion in Colloid & Interface Science.—2015.—Vol. 20, No 3.—P. 183-191.

Numerous fluorocarbon compounds—"fluorocarbon oils" (perfluorocarbon amines (FC-40, FC-70), perfluorocarbons (perfluorooctane, perfluorodecalin), perfluorocarbon ethers (HFE-7100, HFE-7500) and their mixtures (FC-77) serve as a more convenient alternative to mineral oil. Among all technical liquids, fluorocarbon oils have the highest gas permeability, which ensures effective respiration of cells in droplets. In addition, they represent an "alternative phase", i.e. have extremely low solubility in water, hydrocarbons and fats, which leads to their inertness and biocompatibility.

Having a density of 1.6-1.9 g/ml, significantly higher than the density of water, fluorocarbon oils form a double emulsion prone to sedimentation, which makes it easy to collect and re-inject. Stabilization of biocompatible fluorocarbon microfluidic emulsions can be carried out using non-ionic fluorocarbon surfactants. See Holtze C., Rowat A. C., Agresti J. J., Hutchison J. B., Angile F. E., et al. Biocompatible surfactants for water-in-fluorocarbon emulsions. //Lab on a Chip.—2008.—Vol. 8, No 10.—P. 1632-1639. The resulting drops are highly stable and can play the role of universal microcompartments. They provide survival and growth of yeast cells, as well as human cell lines (both suspension Jurkat and adhesive HEK293T) and growth, development and reproduction of encapsulated multicellular organisms C. elegans. See Holtze et al.; and Clausell-Tormos J., Lieber D., Baret J.-C., El-Harrak A., Miller O. J., et al. Droplet-Based Microfluidic Platforms for the Encapsulation and Screening of Mammalian Cells and Multicellular Organisms. //Chemistry & Biology.—2008.—Vol. 15, No 5.—P. 427-437.

The directed manipulation of a single drops in the chip channels opened up a fundamentally new look at the possibilities of microfluidics for ultrahigh-throughput screening of activity. See Ahn K., Kerbage C., Hunt T. P., Westervelt R. M., Link D. R., et al. Dielectrophoretic manipulation of drops for high-speed microfluidic sorting devices. //Applied Physics Letters.—2006.—Vol. 88, No 2.—P. 024104; and Baret J.-C., Miller O. J., Taly V., Ryckelynck M., El-Harrak A., et al. Fluorescence-activated droplet sorting (FADS): efficient microfluidic cell sorting based on enzymatic activity. //Lab on a Chip.—2009.—Vol. 9, No 13.—P. 1850-1858. In previous studies, there was no selection based on the analysis of activity in an individual drop. At the same time, the advantage of microfluidic technologies lies in the ability to carry out a full cycle of selection of improved biocatalytic activity in the chip. See Agresti et al. The application of a microfluidic platform for encapsulation of individual yeast cells in droplets of a biocompatible emulsion, their incubation and sorting in the chip allowed screening of cell activity with a throughput of more than 2000 events per second.

The application of a similar microfluidic platform for the directed evolution of the Pseudomonas aeruginosa aryl sulfatase resulted in a 6-fold increase in its catalytic activity toward synthetic fluorogenic phosphonate in a single round of selection from the library of about $10^6$ variants. See Kintses et al. In this work, the most active variants were selected with a throughput of about 1000 events per second, based on individual activity of cell lysates of single bacterial cells in droplets. The screening procedure was based on the expression of the recombinant enzyme in Escherichia (E. coli) cells, their subsequent lysis and re-transformation for the next rounds of selection. Thus, unlike the previous one, this platform has several drawbacks that limit its practical application.

The application US No 2016/0169788 is known. It describes the composition of the oil phase used to generate biocompatible emulsion, which coincides with the oil phase used in this application. However, a single emulsion is used in application US No 2016/0169788.

SUMMARY OF THE INVENTION

The objective of the invention is the universal platform for ultrahigh-throughput screening using the principle of in vitro compartmentalization in droplets of double emulsion. To solve this problem we created the method for ultrahigh-throughput screening of biological objects, based on the microfluidic generation of droplets, which ensures their monodispersity. The monodispersity of the emulsion, in turn, leads to the uniform concentrations of reagents, as well as the same reaction conditions in the droplets, which reduce the signal-to-noise ratio dramatically during the screening process, i.e. increase the sensitivity and the specificity of selection. Microfluidic emulsion generation provides mild encapsulation conditions, which, in turn, enable its application for encapsulation of living cells. Precisely controlled generation conditions allow encapsulation of a given number of cells or other microbiological objects in double emulsion droplets.

DETAILED DESCRIPTION OF THE INVENTION

Figure 1:
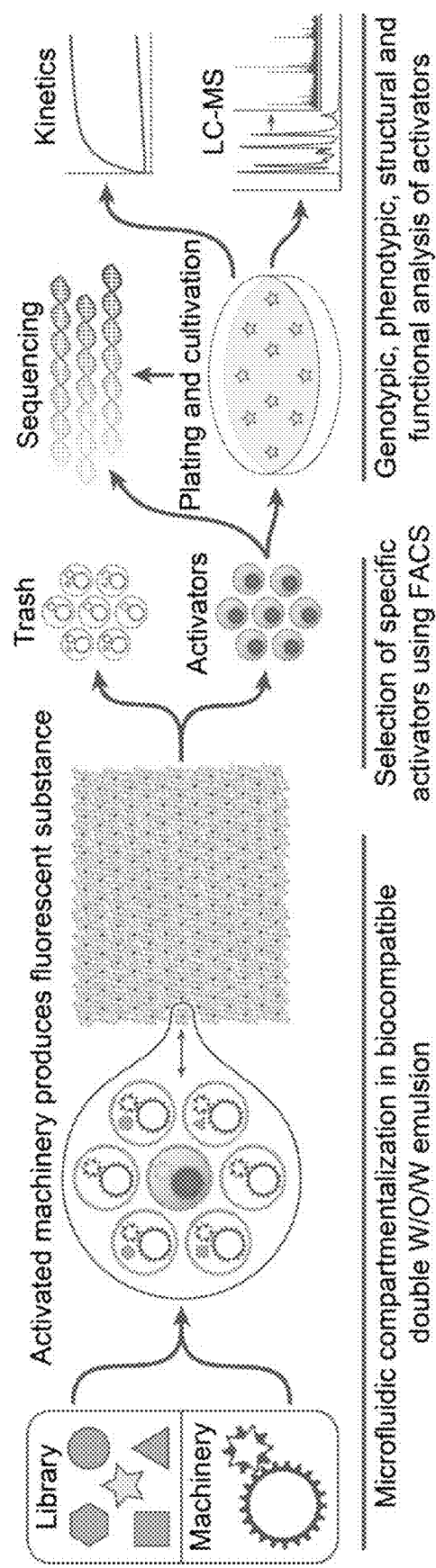
FIG. 1. Microfluidic platform for ultrahigh-throughput screening in droplets of microfluidic double emulsion.

In order to provide ultrahigh-throughput screening in droplets of microfluidic double emulsion (FIG. 1), it is necessary to use some highly specific mechanism activated by the desired phenotype. The activated mechanism should lead to a change in the fluorescence used as an analytical signal. The microfluidic compartmentalization of the library of phenotypes together with the mechanism in droplets of a biocompatible double water-in-oil-in-water (W/O/W) emulsion results in many individual microcompartments in which the mechanism can be activated, leading to a change in fluorescence. Thereafter, activator phenotypes are selected using fluorescence activated cell sorting (FACS), after which they can be analyzed by high-throughput sequencing directly without cultivation (which is crucial in the case of unculturable and slow-growing microorganisms) or subjected to cultivation. Cultivable activator phenotypes are subsequently characterized by genotypic, phenotypic, structural and functional analysis.

Figure 2:
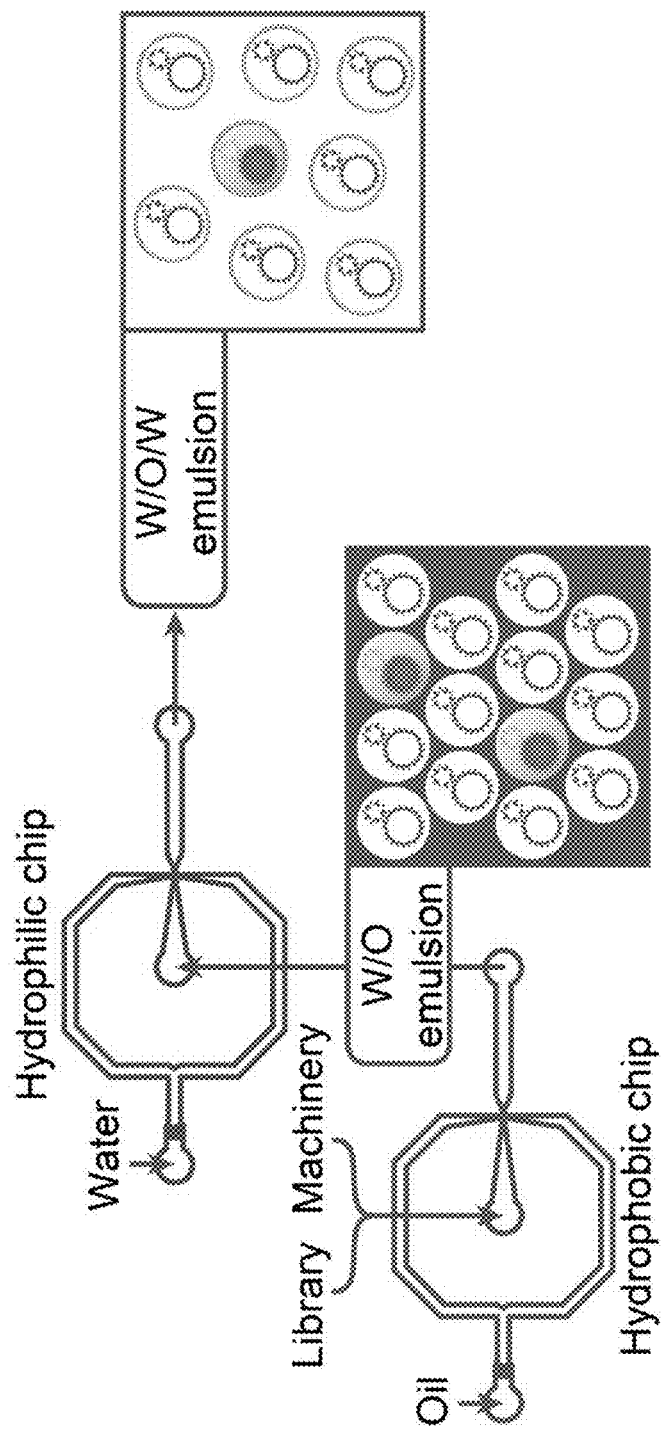
FIG. 2. Generation of double microfluidic emulsion by sequential emulsification in microfluidic chips.

The generation of a microfluidic double emulsion was carried out by the method of sequential emulsification in microfluidic chips (FIG. 2). The pressure controller supplied compressed air to four reservoirs with liquids: an aqueous phase carrying a library of phenotypes; water phase carrying mechanism; oil phase and external aqueous phase. The pressure of compressed air forced the fluids to flow through the teflon tubes leading to the chip. The flow rate of the fluids was determined by the flow controllers connected by a feedback loop to the pressure controller. Thus, the controller automatically maintained the set flow rate by increasing or decreasing the pressure in the reservoirs. Immediately before entering the chip, streams of water phases carrying a library of phenotypes and a mechanism were combined and entered into a hydrophobised chip.

In the hydrophobic chip, the combined internal aqueous phase stream was split into separate droplets in the oil phase stream, and the resulting single water-in-oil emulsion entered to the hydrophilic chip. In the hydrophilic chip, the water-in-oil emulsion flow was split into separate droplets of a double water-in-oil-in-water (W/O/W) emulsion in a flow of external aqueous phase.

The solution of phosphate-buffered saline, Tris-HCl, ions of divalent metals, growth media could be used as the internal aqueous phase. Mineral oil supplemented with 3% of the emulsifier Abil EM 180 or 2% Pico-Surf2 in Novec7500 fluorocarbon oil can be used as the oil phase. The external aqueous phase may contain 50 mM sodium or potassium phosphate buffer, 2% Pluronic and 0.1% Mowiol 23-88.

The channels of the chips must have a higher wettability with respect to the dispersion medium, otherwise the emulsion generation is unstable. Hydrophobizers (trichlorooctadecylsilane or Aquapel) were used for chemical modification while for stabilization of the hydrophilic surface polyvinyl alcohol was used. Mineral oil or fluorocarbon oil was used as the oil phase. Mineral oil has a high viscosity, reduces the transport of gases and leads to a floating emulsion, which complicates its use. In turn, the fluorocarbon oils HFE-7500 and FC-40 had a much lower viscosity, that enable to use them for generation of a double emulsion with a diameter of 20 µm. High gas permeability of fluorocarbon oils was used for screening combined with cultivation, and high density results in the formation of a sedimentation emulsion, more convenient for screening procedure.

In order to ensure the biocompatibility of the emulsion, high molecular weight surfactants with extremely low interfacial transport capacity were used: Abil EM 180 for mineral oil, Pico-Surf 2 for fluorocarbon oil and Pluronic F-127 for the external aqueous phase. The destruction of the emulsion selected after FACS was mediated by its drying on a plate with a semi-solid culture medium, which resulted in 90±20% survival of the yeast cells.

Figure 3:
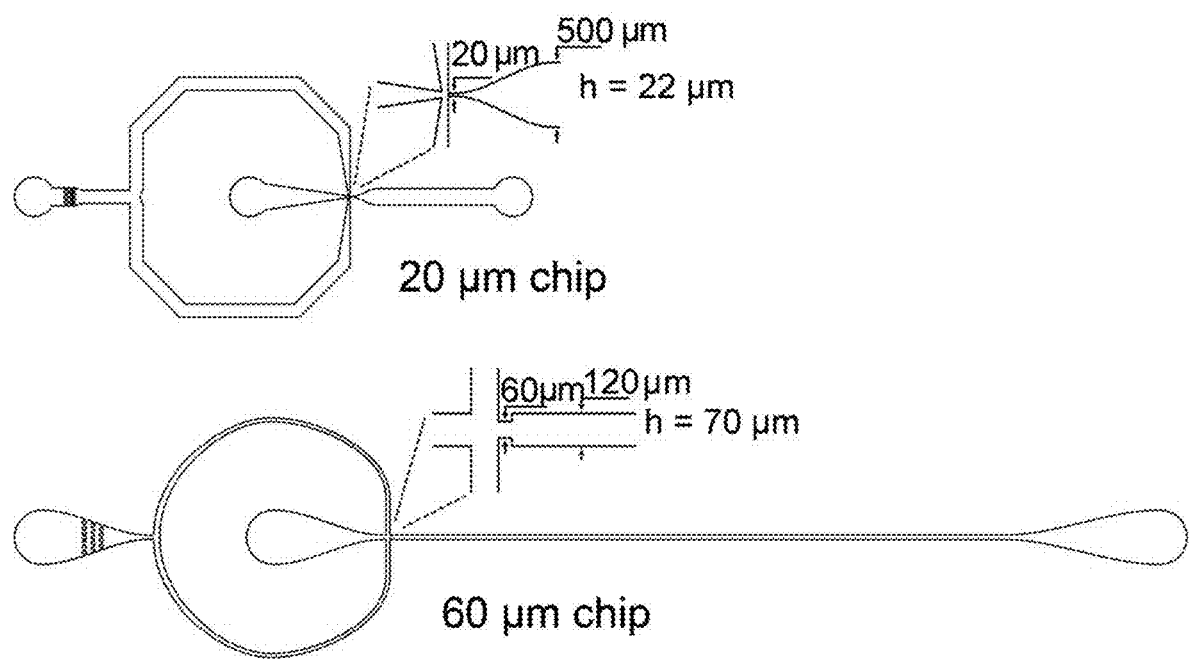
FIG. 3. The design of microfluidic chips used for screening of biocatalytic and antimicrobial activity.

Microfluidic polydimethylsiloxane chips, obtained using soft lithography technology (FIG. 3) were used for microfluidic compartmentalization. The utilization of two chips for a single emulsification was much more simple than application of a single chip for generating a double emulsion, due to their interchangeability and straightforward chemical modification technology. The splitting of the dispersed phase occurred at the chip nozzle, where flows of immiscible liquids were joined.

Figure 4:
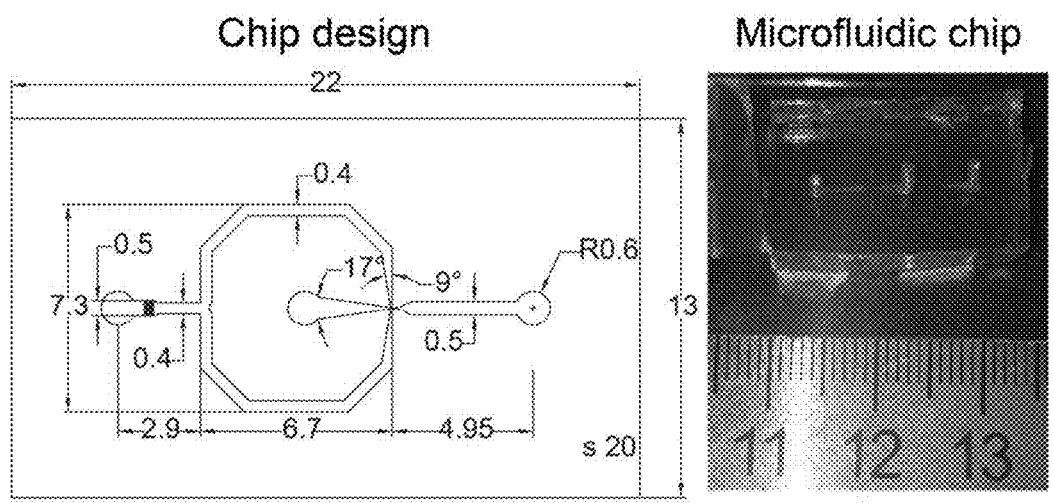
FIG. 4. Microfluidic chip for generation of 20 μm droplets, applied for encapsulation of cells in double emulsion droplets: scheme (top left) and photo (top right) of the general design of the microfluidic chip. Scheme (bottom left) and microscopy (bottom right) of the orifice of a microfluidic chip. Bar size (lower left corner) 0.1 mm.
Figure 4:
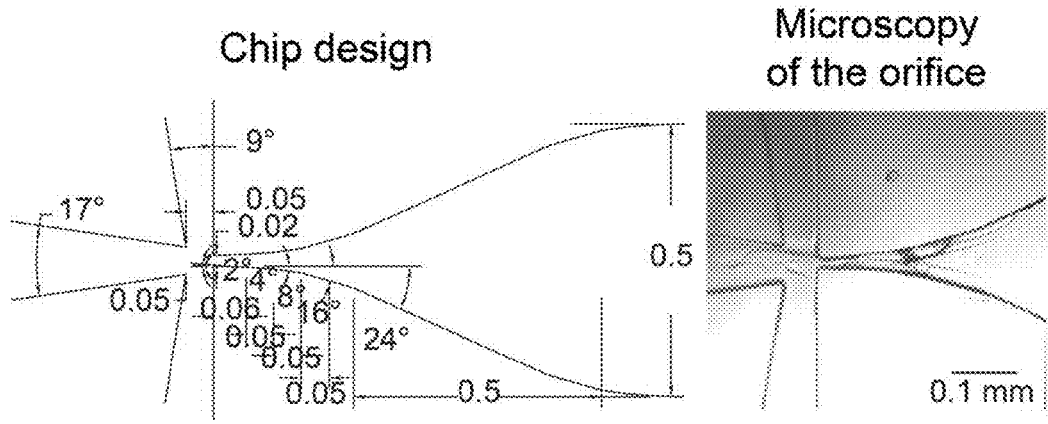
Figure 5:
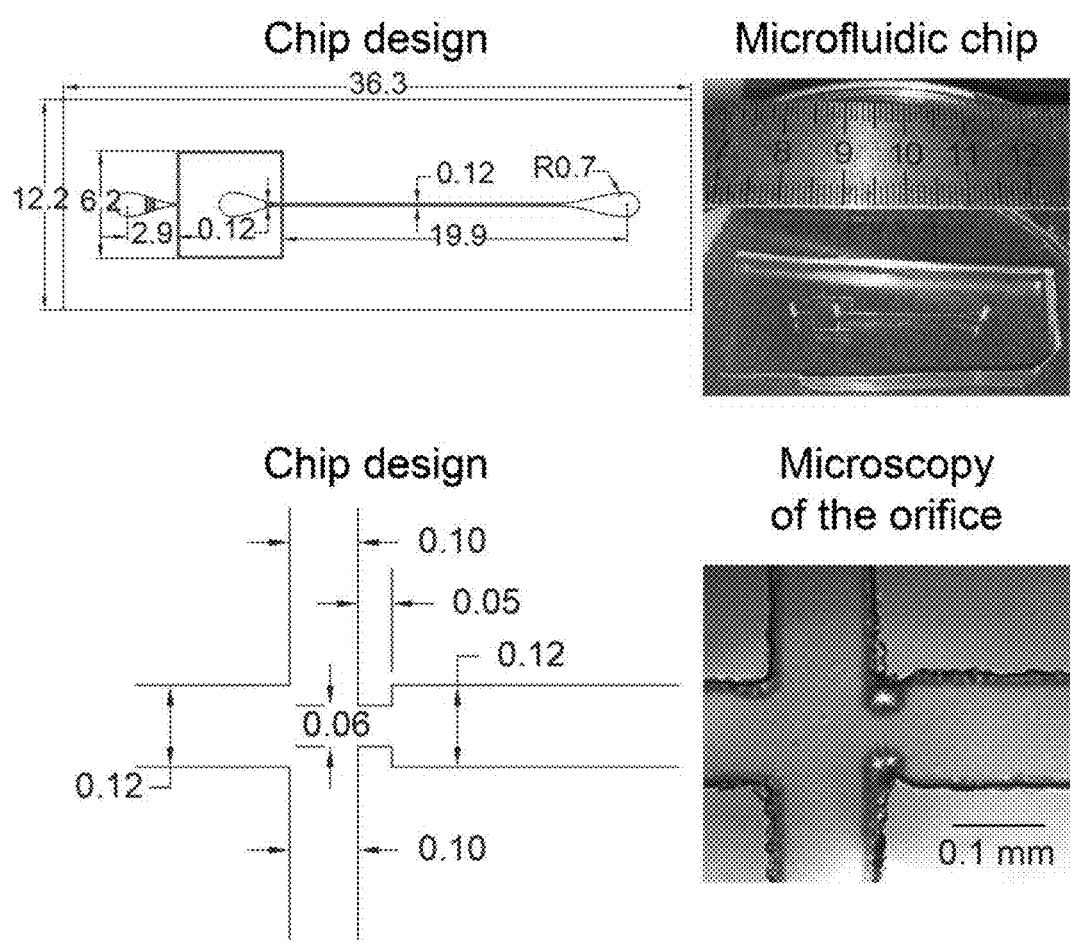
FIG. 5. Microfluidic chip for generation of 60 μm droplets, applied for encapsulation of cells in double emulsion droplets: scheme (top left) and photo (top right) of the general design of the microfluidic chip. Scheme (bottom left) and microscopy (bottom right) of the orifice of a microfluidic chip. Bar size (lower left corner) 0.1 mm.

The chips had a 20 µm (FIG. 4) and 60 µm (FIG. 5) channels, which made it possible to generate a double microfluidic emulsion with a diameter of 20-90 µm. Reduction in the size of the channels results in an increase in throughput. The generation of microfluidic double emulsion occurred with a throughput up to 25000 events per second in the chip with 20 µm channels and 3000 events per second in the 60 µm chip.

Figure 6:
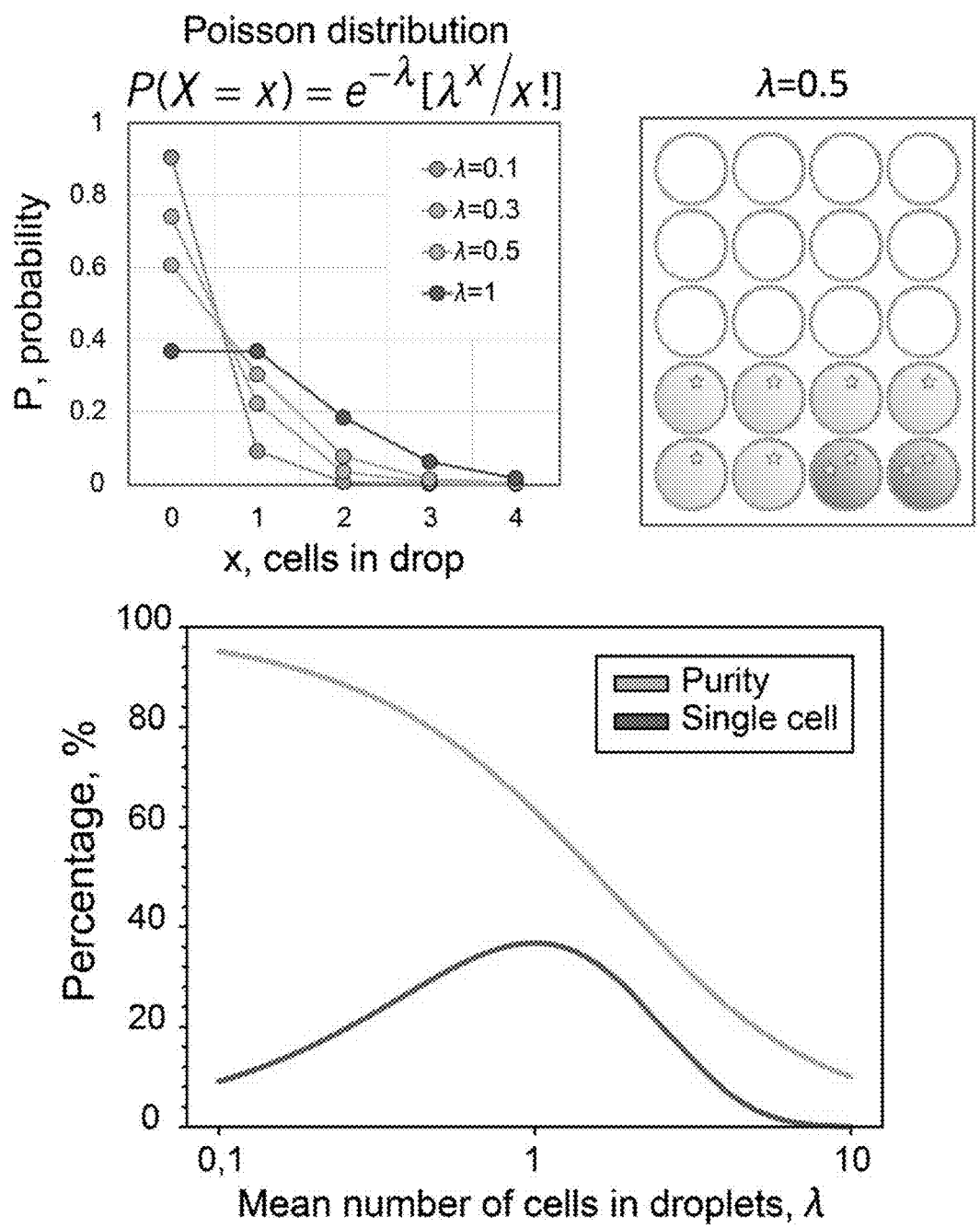
FIG. 6. Distribution of cells encapsulated in droplets of microfluidic double emulsion.

As it was mentioned previously, discrete microscopic objects are encapsulated in microfluidic droplets in accordance with the Poisson distribution (FIG. 6) due to the monodispersity of the microfluidic double emulsion. Thus, the lower the degree of filling. (the average number of cells in droplets), the higher the purity of selection resulted from the reduction of probability of coencapsulation of two or more cells into one droplet.

Simultaneously, at $\lambda<0.3$, the proportion of droplets filled with cells rapidly decreases, which reduces the efficacy of screening. For $\lambda=0.1$, droplets carrying one cell represent 95.1% of the total number of filled droplets, however, 90.5% of the drops remain empty. Thus, to achieve a compromise between purity and screening efficacy, the most optimal is the range $0.3<\lambda<0.7$. For screening of biocatalysts, the filling degree $\lambda=0.5$ was used, which corresponds to the maximum purity of selection of 78.7%. On the other hand, if it is required that all the drops are filled (which was used for S. aureus cells in the case of selection of antibiotic activity), it is necessary to use $\lambda\gg1$. For $\lambda=10$, used to fill the droplets with S. aureus cells, the proportion of empty droplets is <0.005%.

Screening Biocatalytic Activity in Droplets of Microfluidic Double Emulsion.

Yeast Display of Biocatalysts and Highly Sensitive Detection of Biocatalytic Activity.

Figure 7:
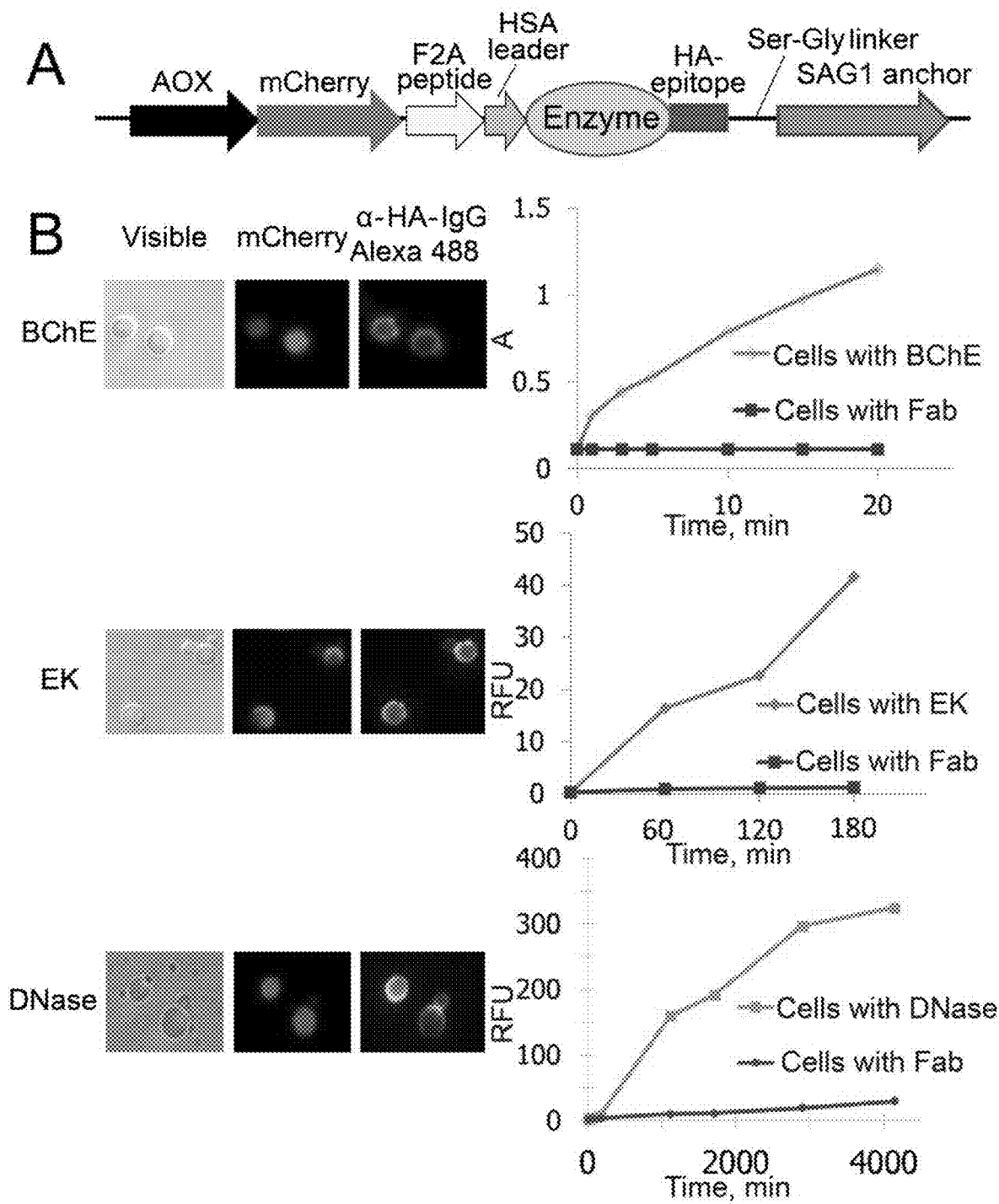
FIG. 7. Yeast display of biocatalysts.

Previously, screening of biocatalysts in droplets based on the principle of in vitro compartmentalization was carried out with approaches based on in vitro transcription/translation, lysis of individual bacterial cells in droplets, as well as bacterial and yeast display. See Agresti et al. Of all the above, the yeast display is the most versatile approach, as it enable folding of complex proteins, formation of correct disulfide bonds, as well as their glycosylation, which was of fundamental importance in the case of rhBChE, which production in the active form is possible only in eukaryotic cells. In order to simplify the identification of the cells that have activity in model experiments, we used the red fluorescent reporter protein mCherry. Simultaneously, it is necessary that the amount of mCherry and the enzyme correlate. To do this, their expression was carried out using a single promoter, and the coding sequences of mCherry and the enzyme were separated by a "self-processing" F2A peptide, providing simultaneous mCherry and enzyme production using a single mRNA transcript mediated by the ribosome skipping. Thus, the genetic construct used for the yeast display of biocatalysts (FIG. 7A) contained the methanol inducible AOX1 alcohol oxidase promoter, the sequence of the red fluorescent reporter protein mCherry, the "self-processed" F2A peptide, the leader peptide of human serum albumin (HSA) for extracellular transport, the enzyme, the hemagglutinin epitope (HA) for immunofluorescent detection of the anchored enzyme and the sequence SAG1, connected by a serine-glycine linker, providing the anchoring of enzyme on a yeast cell.

Three different enzymes demonstrating phosphodiesterase (deoxyribonuclease I—DNase), protease (enteropeptidase—EK) and esterase (butyrylcholinesterase—BChE) activity (FIG. 7B) were used to demonstrate the versatility of the platform. Immunofluorescent staining indicated that all three enzymes were produced in an anchored form (a fluorescence halo was observed) on the surface of yeast cells. At the same time, mCherry localized intracellularly (uniform fluorescence of cells was observed). The yeast producing anchored enzymes and the control yeast producing the Fab antibody fragment were analyzed for biocatalytic activity using appropriate substrates (Ellmann reagent in the case of BChE, Gly-(Asp)4-Lys-naphthylamide in the case of EC and 5'FAM-AAAAAAACCCCCC-CATATAGCGCGTTTTTTT-3'RTQ1 (SEQ ID NO: 1) in the case of DNase) and it was shown that all biocatalysts were produced in an active form.

Figure 8:
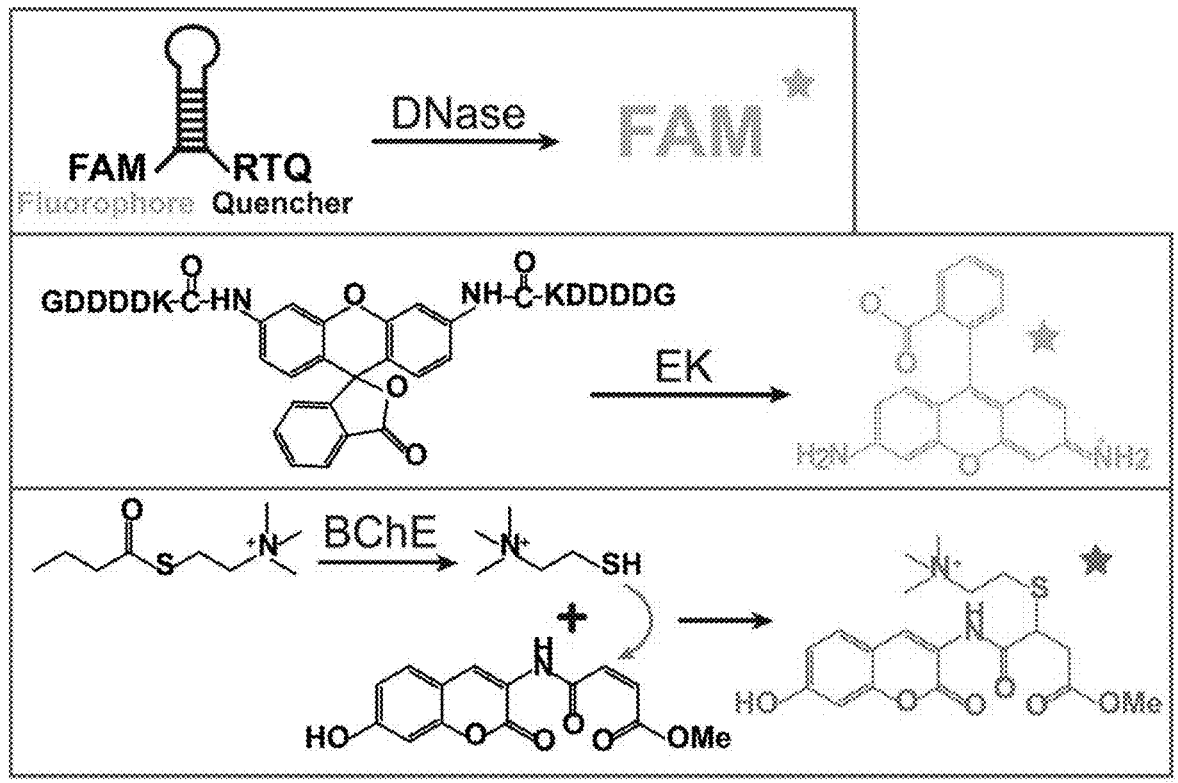
FIG. 8. Schemes and kinetic constants of enzymatic reactions, applied for screening of biocatalysts in droplets.

For screening in droplets, it is necessary that the enzymatic reaction product has a high hydrophilicity (which limits its transport through the oil layer to the external aqueous phase), as well as a fluorescence excitation/emission spectrum corresponding to the excitation lasers and emission filters of the cell sorter. Yeasts carrying anchored enzymes had a red fluorescent reporter protein. Hence, green (530/30 nm) and blue (450/50 nm) fluorescence was used to monitor the product. For the three enzymes, different fluorogenic substrates (FIG. 8) were used, based on FRET-pair, non-fluorescent amide, and a conjugate reaction, in which the product of the classical reaction catalyzed by BChE reacted with the non-fluorescent substrate to form a fluorescent adduct. The enzymes had different catalytic efficiencies ranging approximately 100 times toward these fluorogenic substrates. For the suspension of cells with anchored biocatalyst, the ratio of the rates of enzymatic and spontaneous hydrolysis ranged from 550 to 85, resulted in a signal-to-noise ratio of 33 to 6.5 when the reaction was performed in 384-well plates. Immunofluorescent staining and cytometry with fluorescent beads carrying a standard numbers of fluorophore showed that there are 7000±3000 molecules of biocatalysts on the surface of one yeast cell, which made it possible to evaluate the enzymatic constants of anchored biocatalysts.

Selection Efficiency of Biocatalysts from a Mixture of Active and Inactive Cells.

Figure 9:
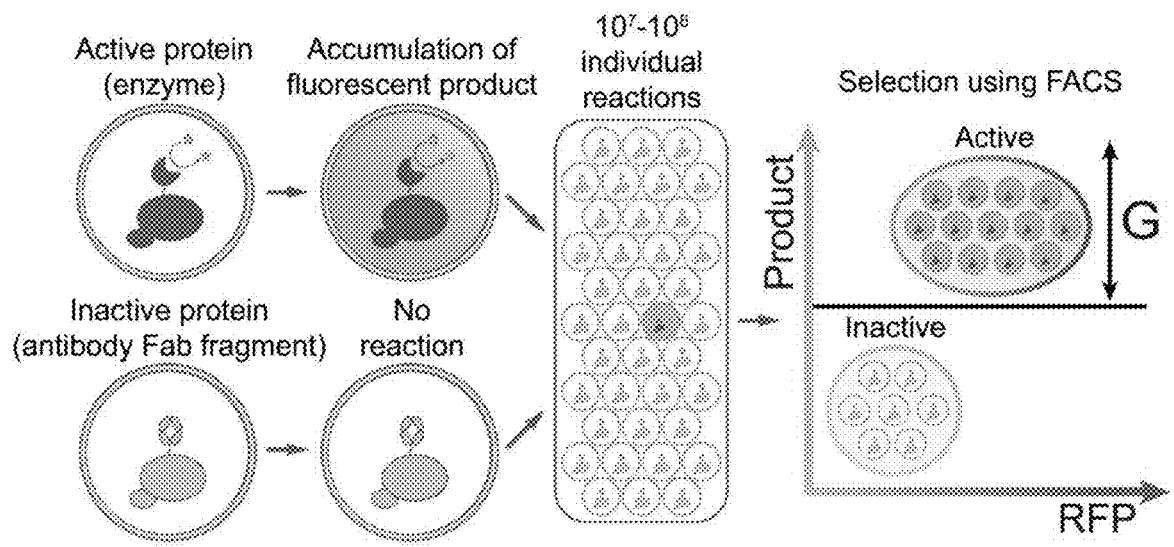
FIG. 9. The principal scheme of platform for ultrahigh-throughput screening of biocatalysts in double emulsion droplets.
Figure 10:
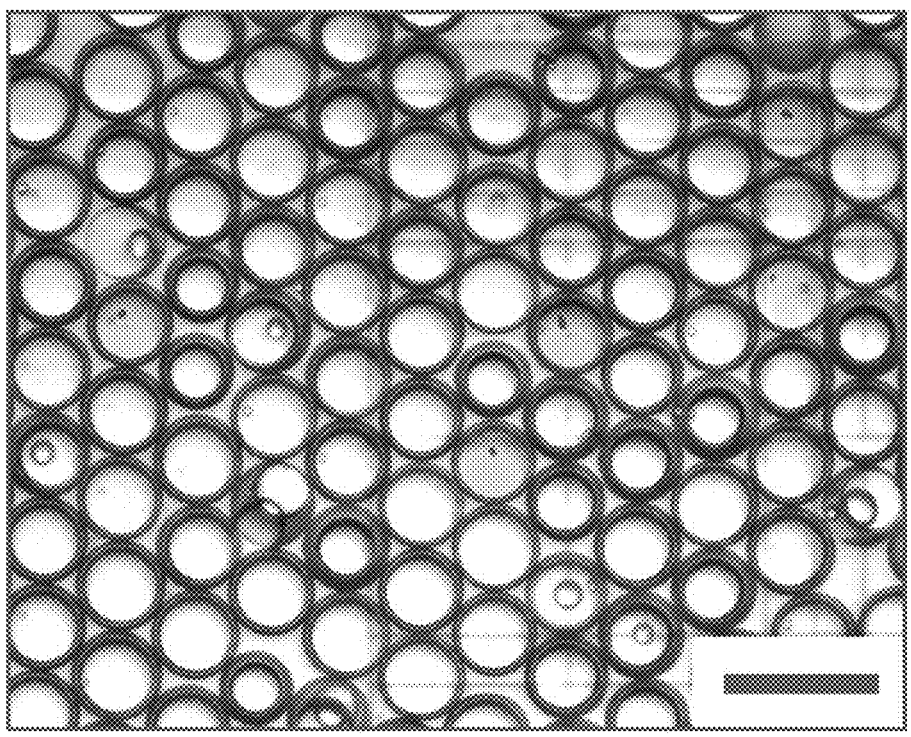
FIG. 10. Microscopy of a mixture of 1:10 active and inactive cells. The image was obtained by overlay of visible light and fluorescence microscopy using green fluorescence of product of the enzymatic reaction and the red fluorescence of mCherry fluorescent protein. The scale bar is 100 μm.

To assess the efficiency of screening of biocatalysts, we used artificial mixtures of active (producing anchored enzyme and red fluorescent reporter protein mCherry) and inactive (producing Fab fragment of the antibody without of the fluorescent reporter) yeast cells (FIG. 9). The compartmentalization of a mixture of active and inactive cells together with a fluorogenic substrate in droplets of a microfluidic double emulsion result in the formation of two populations with different levels of product fluorescence. Selection of droplets with the highest level of fluorescence using FACS led to enrichment with active cells. The microfluidic emulsion was highly monodisperse (FIG. 10), and the accumulation of the reaction product occurred exclusively in droplets carrying active yeast cells.

Figure 11:
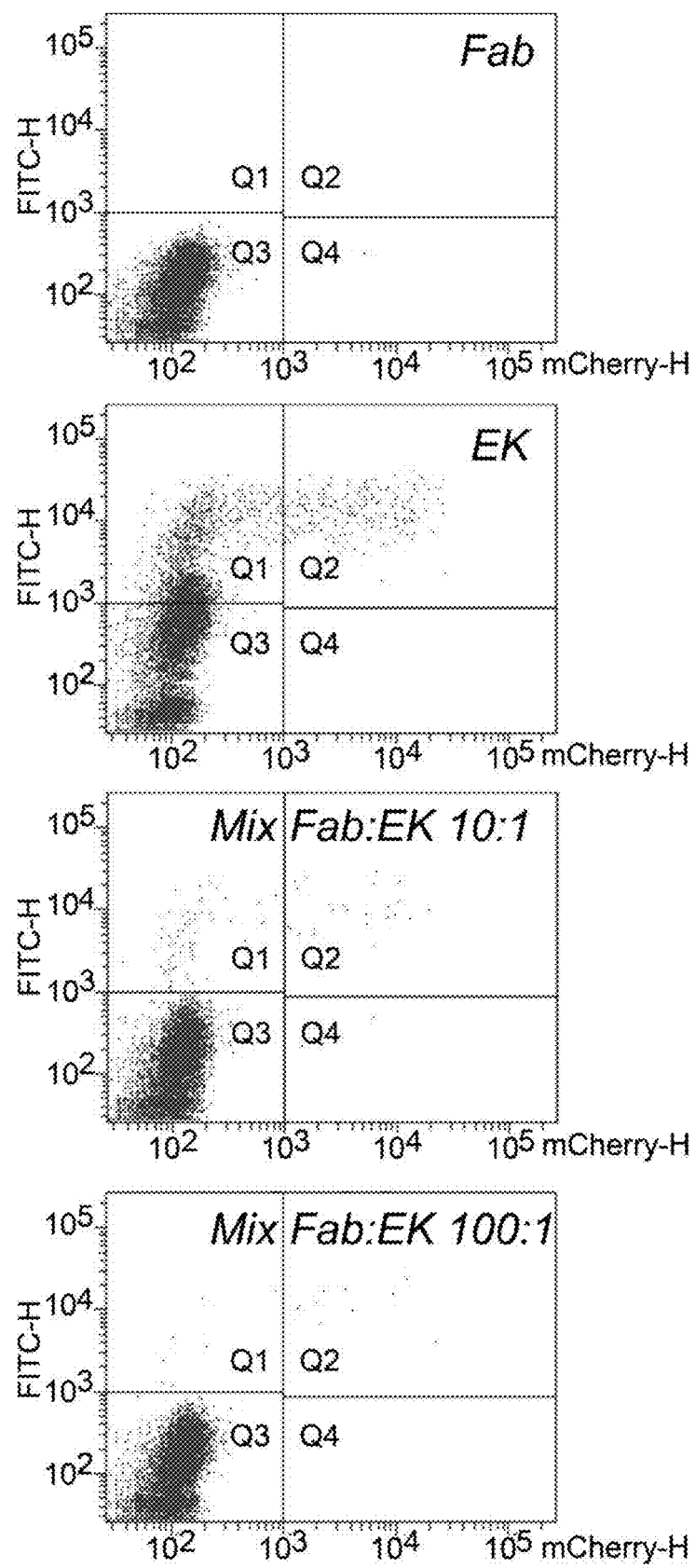
FIG. 11. The flow cytofluorimetry of double emulsion droplets with encapsulated cells carrying the antibody Fab fragment, biocatalyst and artificial libraries containing 10% and 1% of active cells with anchored biocatalyst using the EK as an example.

The model screening of artificial libraries of biocatalysts was conducted in order to evaluate the selection efficiency (the degree of enrichment) for each biocatalyst after ultrahigh-throughput screening of droplets of a water-in-oil-in-water emulsion using FACS. Four samples were encapsulated together with the corresponding fluorogenic substrate under the same conditions: 1) yeast with anchored antibody Fab fragment (drops in which only the background level of the reaction occurs), 2) yeast with anchored biocatalyst (drops in which only the catalytic hydrolysis of the substrate takes place) 3) Biocatalyst/Fab 1:10 mixture, 4) Biocatalyst/Fab 1:100 mixture. After encapsulation, the samples were was analyzed and sorted using a BD FACSAria III FACS (FIG. 11).

Figure 12:
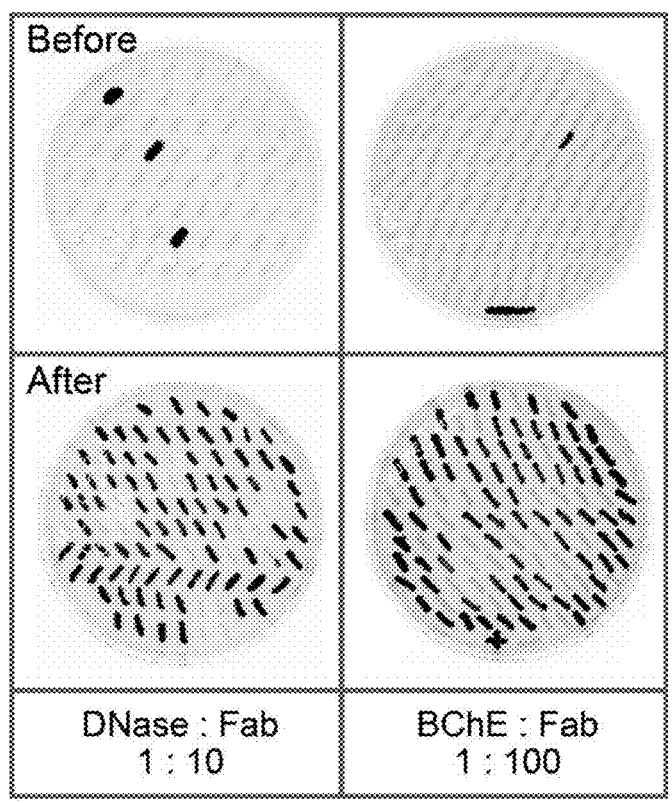
FIG. 12. Plates with clones regenerated from droplets before and after selection using FACS.

The population of droplets with a high level of fluorescence was selected using FACS in the mode of maximum purity of the screening with a productivity in the range of 10 000-20 000 events per second after the reaction took place in drops. The selected droplets were plated on agar plates and after 2-3 days the formation of yeast colonies was observed. Colonies regenerated from drops before and after selection were transferred on plates with methanol, where induction of expression of fluorescent reporter was observed (FIG. 12). As a result, efficient enrichment of each of the biocatalysts was observed.

Figure 13:
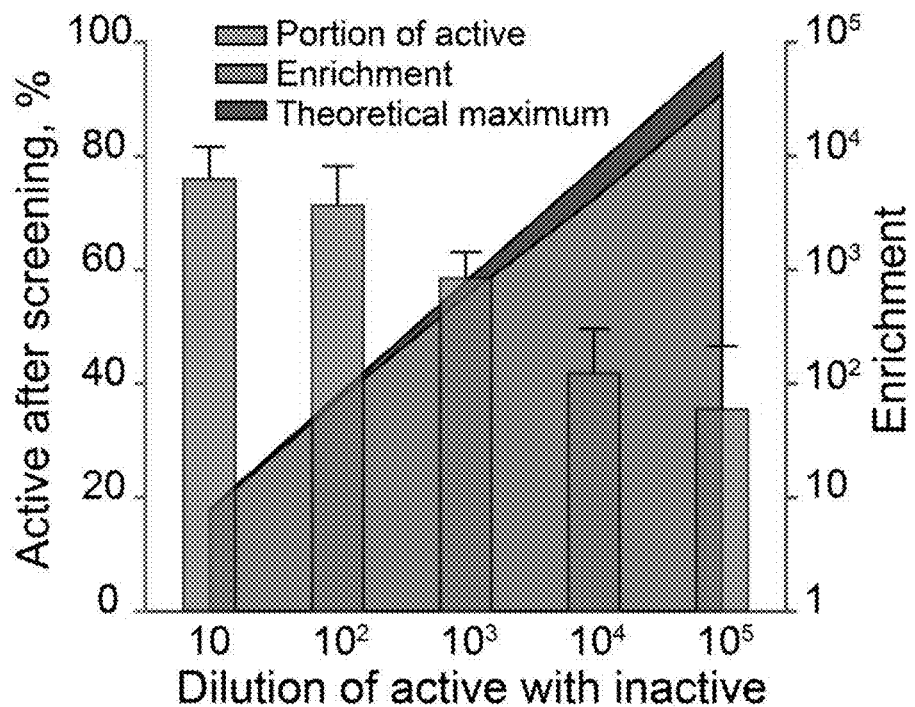
FIG. 13. The dependence of the proportion of active cells and enrichment on the dilution of active cells with inactive ones.

Ultrahigh-throughput screening of droplets was accomplished with different ratios of active and inactive cells in the range of $1:10-1:10^5$ (FIG. 13) in order to determine how the efficiency of screening depends on the ratio of active and inactive cells. The degree of enrichment of active cells from a mixture with inactive was close to the theoretical limit in the case of a 1:10 and 1:100 dilution. Even at extremely high $1:10^5$ dilution, more than 35% of active clones were observed after one round of selection, which is only two times less than the theoretical maximum.

Thus, for cells with biocatalytic activity, an extremely high efficiency of selection from a mixture of active and inactive cells was shown using only one round of screening.

Selectivity of the Selection of Biocatalysts from a Mixture of Biocatalysts with Different Specificity or Different Levels of Activity.

Figure 14:
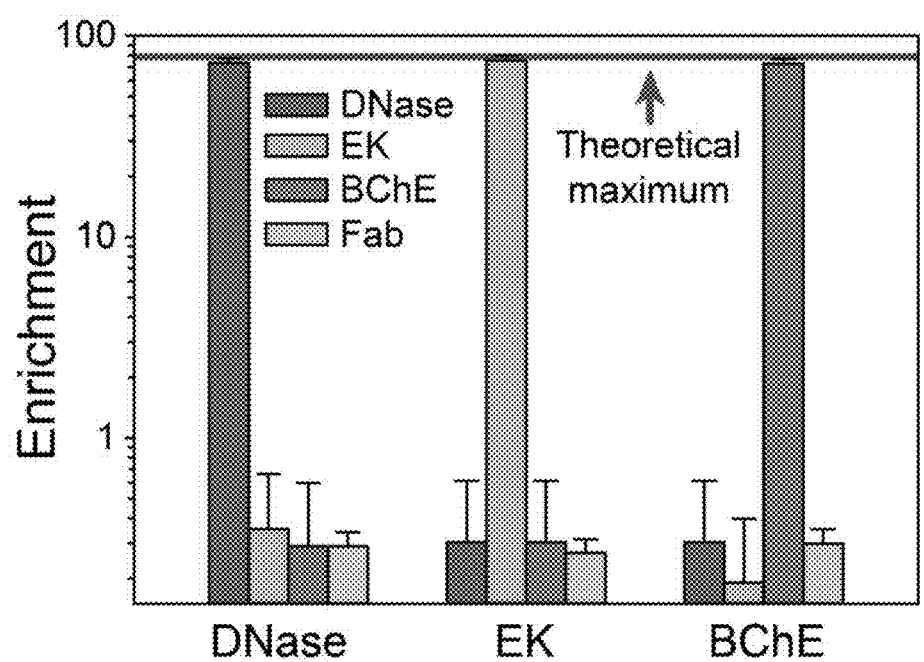
FIG. 14. The specific selection of biocatalysts from a mixture of enzymes.

The "artificial activity library" was used for the screening of biocatalysts from a mixture of cells displaying different enzyme activity and substrate specificity. "Artificial activity library" was prepared by mixing the yeast, carrying separately each of the three biocatalysts previously used and diluted 100 times with inactive cells. Thus, the proportion of cells of each type of activity was less than 1% in the mixture. The activity library was selected for each type of enzymatic activity separately using the corresponding fluorogenic substrate (FIG. 14). Cells with each type of biocatalytic activity were specifically selected for a given enzymatic activity with an efficiency close to the theoretical maximum, without enrichment with cells carrying a different type of activity.

Figure 15:
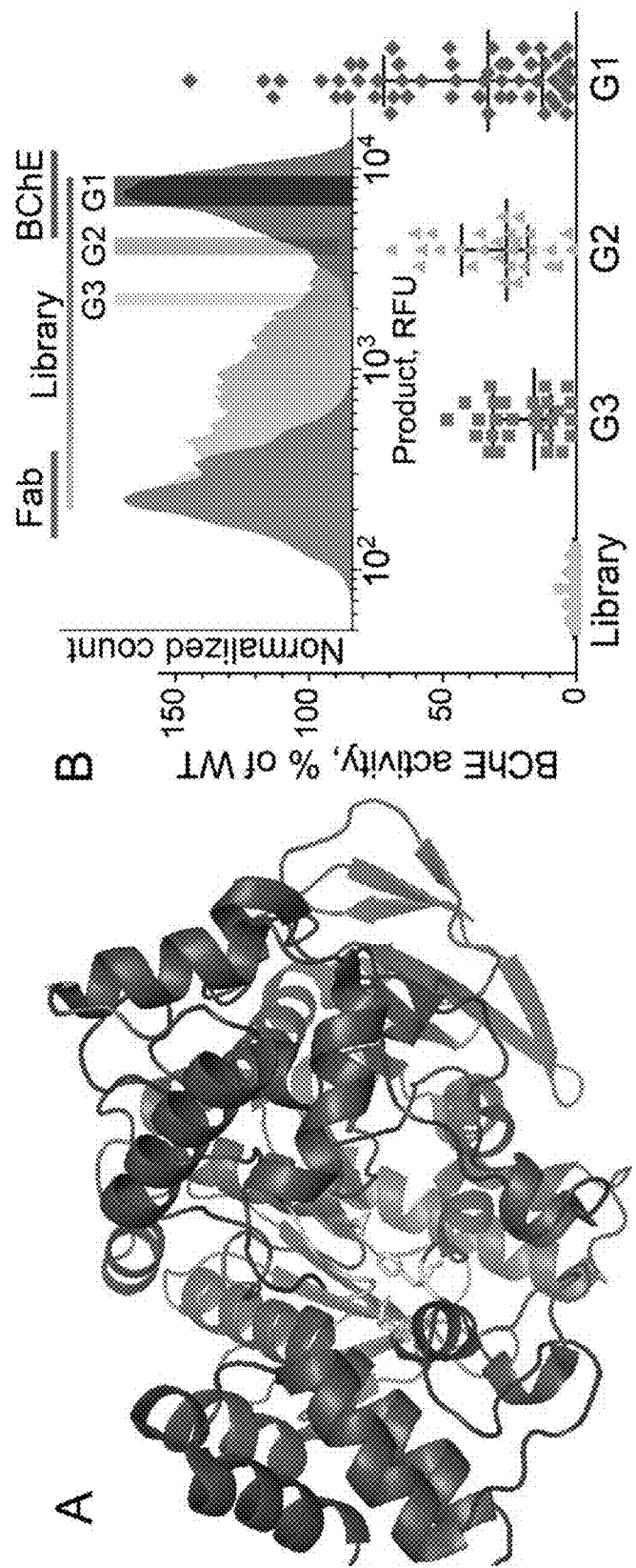
FIG. 15. (A) Crystal structure of BChE. The catalytic triad S198-H438-E325 and the mutated sequence 284-TPLSV-288 is shown in gray and yellow respectively. (B) The activity of individual clones before and after selection using gates G1-G3 with different levels of droplet fluorescence. The inset shows the selection of droplets carrying control cells (gray), the library (red), and wild type (blue) by fluorescence, as well as the fluorescence level of gates G1-G3 used for selection.

The BChE library was used to investigate how the efficiency and selectivity of selection depends on the activity level of the biocatalyst. The representativity of the library was about $3\times10^5$ variants. The BChE library was made by randomization of 5 consecutive amino acids in the sequence of the wild type BChE (WT) 284-TPLSV-288 in acyl-binding loop located close to the active center of enzyme (FIG. 15A). The amino acid substitutions significantly reduced the activity of clones. The average library activity was less than 0.5% of activity of the wild type BChE. The yeast with the anchored BChE mutants were encapsulated together with the fluorogenic substrate in droplets of a microfluidic double emulsion. The resulting drops had different levels of fluorescence. They were selected using three G1-G3 gates with different levels of fluorescence G1>G2>G3 (FIG. 15B).

The analysis of the activity of individual clones obtained before and after selection indicates the efficiency of the selection in the case of using each of the three gates. At the same time, the clones selected from the droplets with the highest level of fluorescence had the highest level of activity. Thus, it was qualitatively shown that the developed platform can be used to select biocatalysts with different levels of the same activity.

In order to quantify the efficiency of selection of with different levels of the same activity, three clones with different levels of BChE activity, selected by biocatalysts using ultrahigh-throughput screening with gates G1-G3 were used. Mutant cl 13, selected from G3, had an insignificant level of activity (1.1% of WT BChE). This activity was approximately 2 times above the background activity of control cells measured in the 384 well plate. Mutant cl 8 and cl 3 were selected from G2 and G1, respectively, and had 5.4 and 55% of the WT BChE activity.

Figure 16:
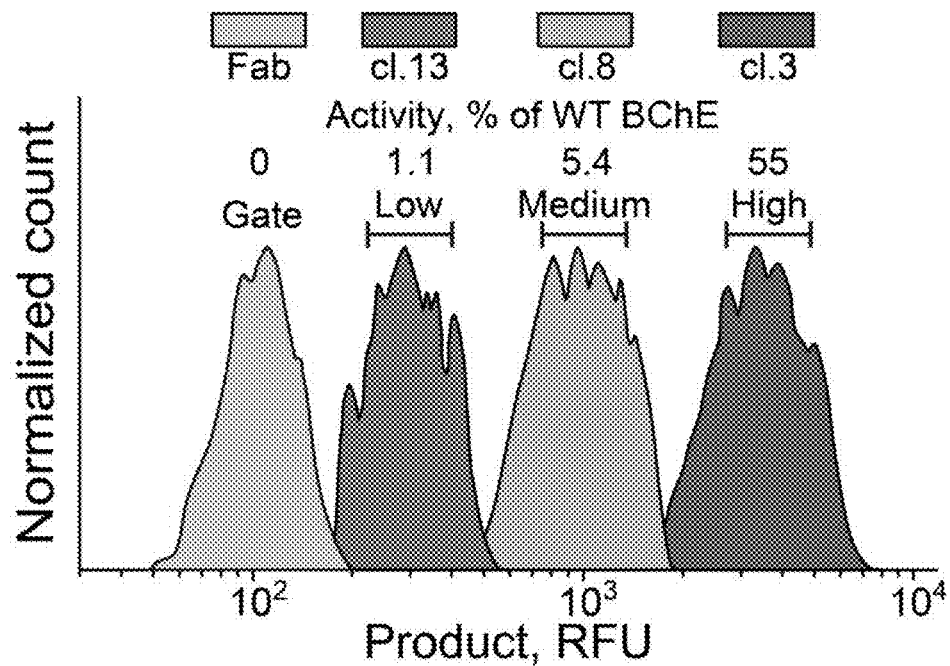
FIG. 16. BChE mutants with different levels of activity result in droplets with different levels of fluorescence.
Figure 17:
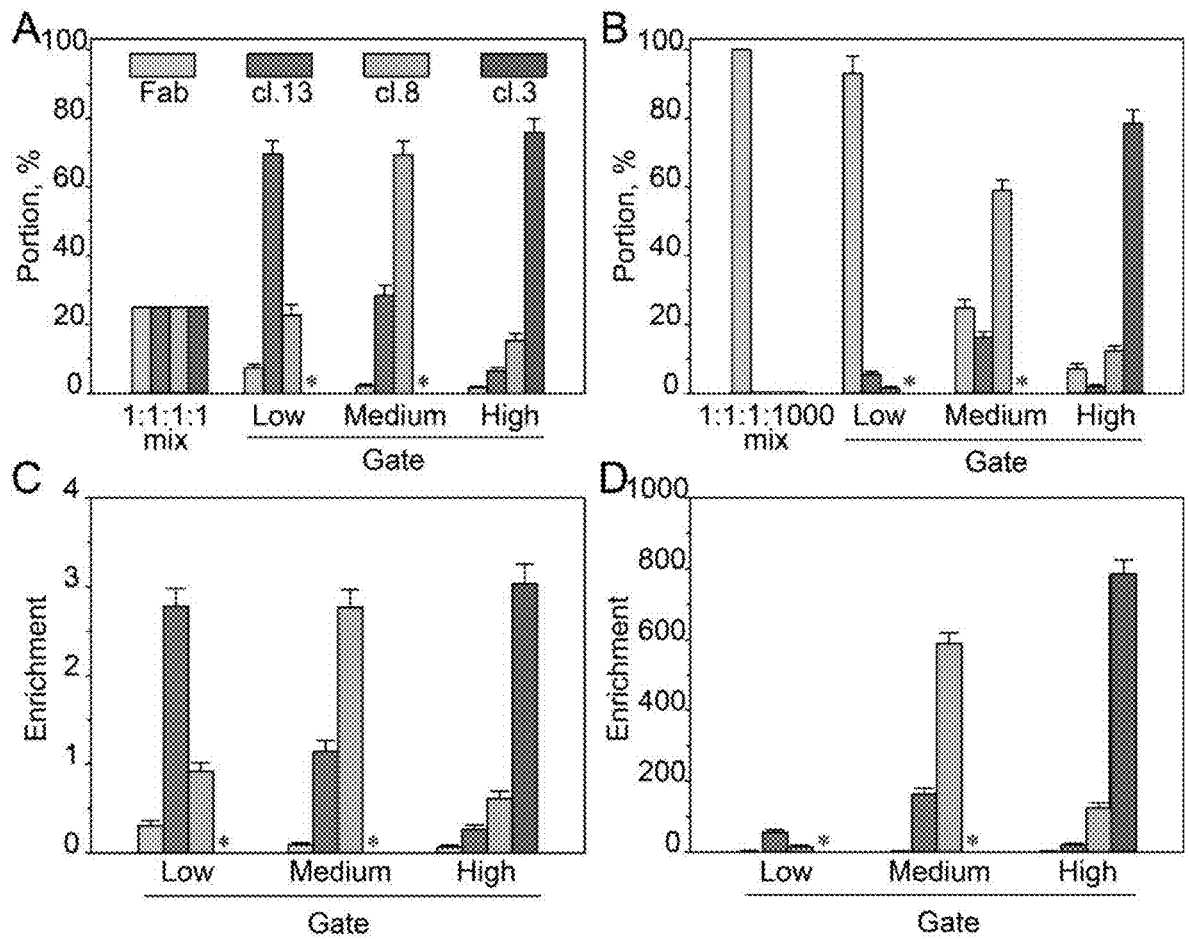
FIG. 17. The selection of BChE mutants with different levels of activity. The proportion of mutants before and after selection (A) for a mixture in 1:1:1:1 ratio and in (B) 1:1:1:1000 ratio, as well as the corresponding enrichment (C) and (D). An asterisk indicates that the clone (cl 3) was not identified in the selected population.
Figure 18:
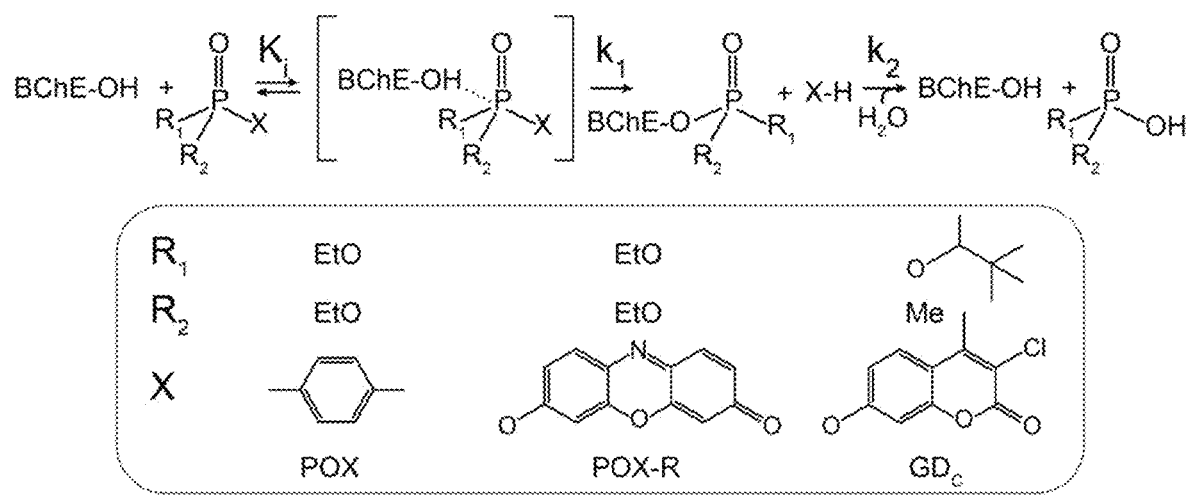
FIG. 18. The scheme of the reaction between and OP, as well as the structures of OPs used. Ki—inhibition constant; k1—phosphylation rate constant; k2—self-reactivation rate constant.
Figure 19:
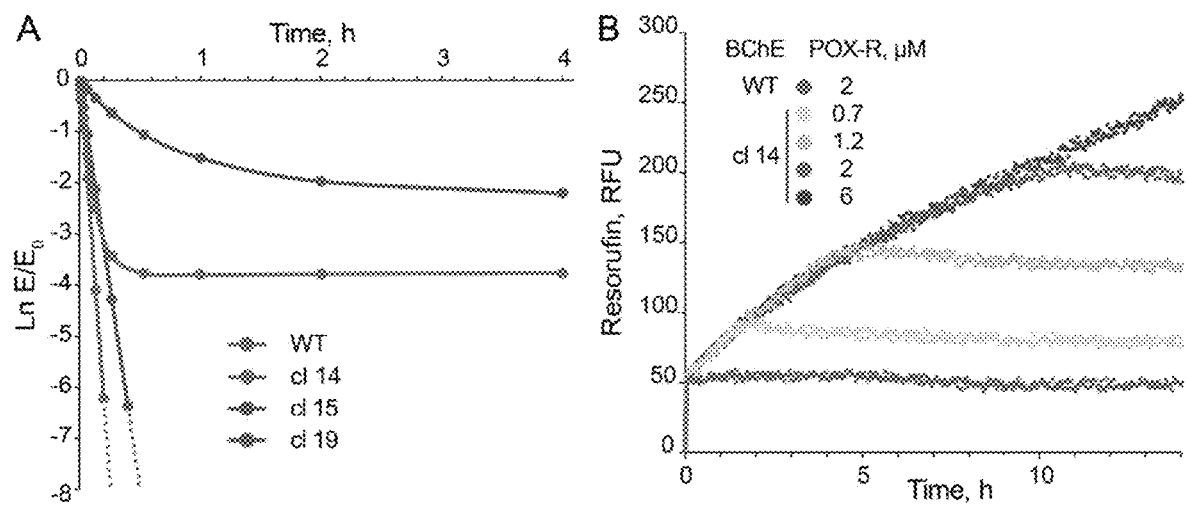
FIG. 19. (A) The kinetics of BChE inhibition by paraoxon using wild type BChE (WT), cl 19 mutant enzyme selected for GDC, and mutants cl 14 and cl 15 selected for resistance against POX. (B) Mutant cl 14, unlike WT, demonstrate catalytic hydrolysis of POX-R. The concentration of both enzymes is 0.45 µM.
Figure 20:
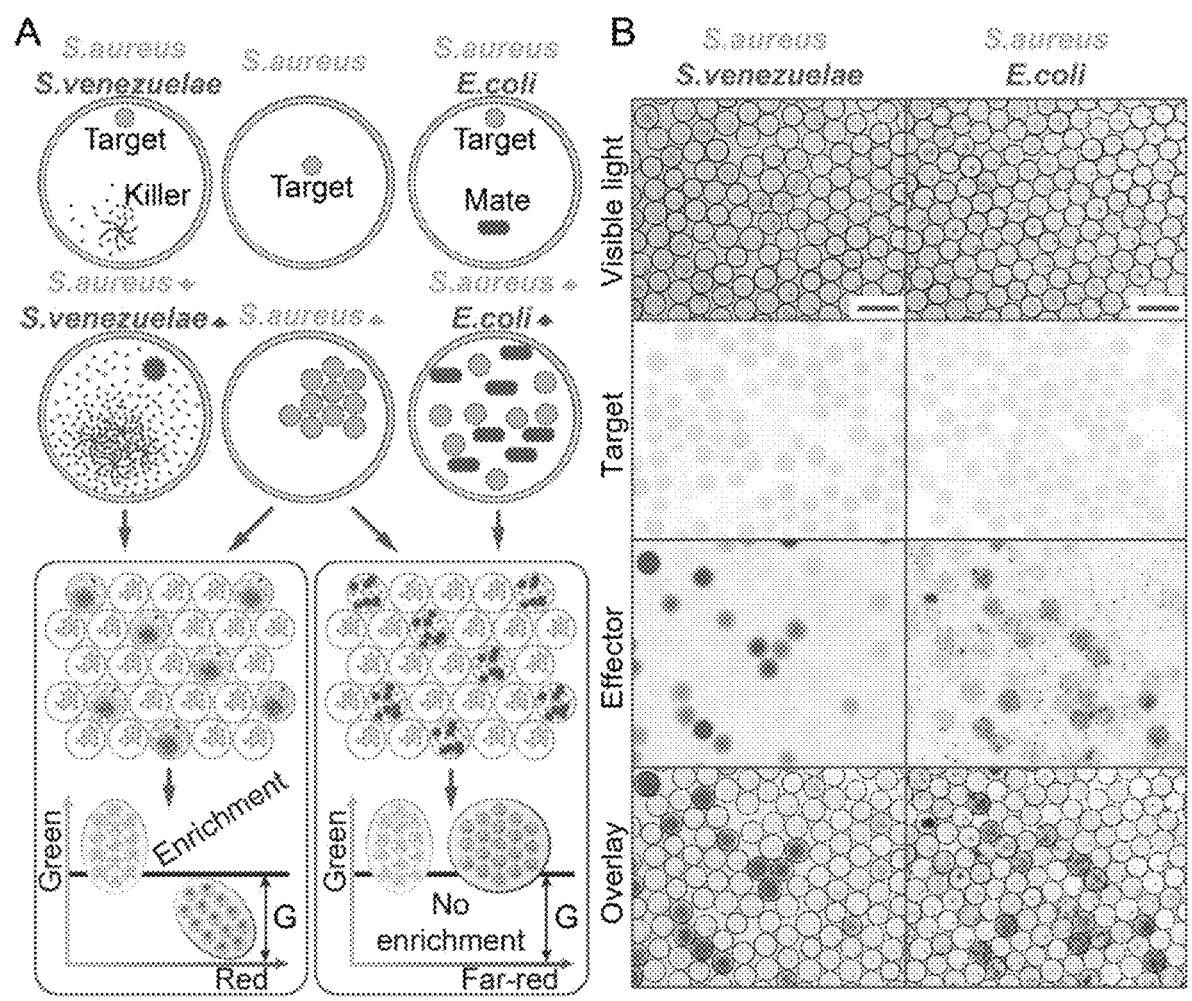
FIG. 20. (A) A screening scheme based on cell-cell pairwise interactions for the selection of bacteria that inhibit *Staphylococcus aureus* (*S. aureus*) growth in droplets of a biocompatible microfluidic double emulsion. (B) Microscopy of droplets with encapsulated *S. aureus*+*S. venezuelae* and *S. aureus*+*E. coli* cells. Visible light microscopy, fluorescence microscopy of green fluorescence *S. aureus* (target), red fluorescence *S. venezuelae* (left effector) and far-red *E. coli* fluorescence (right effector), and overlay. The scale bar is 100 µm.
Figure 21:
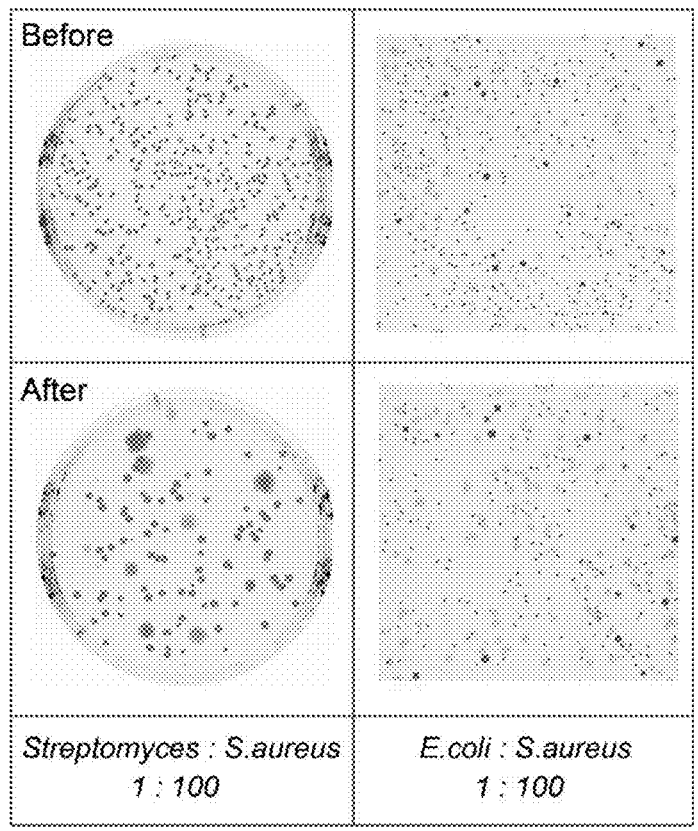
FIG. 21. Plates with bacterial colonies regenerated from droplets before and after selection using FACS-based screening. *S. aureus*, colored with green, were identified based on their green fluorescence, *E. coli*—far-red fluorescence, and *S. venezuelae*—by specific colony morphology.

The compartmentalization of cl 3, cl 8, cl 13 and control cells together with the substrate in the droplets led to the formation of four populations with different levels of fluorescence, corresponding to different levels of accumulated product: cl 3—high, cl 8—medium, cl 13—low (FIG. 16). The BChE mutants cl 3, cl 8 and cl 13, as well as control cells (Fab) were mixed with each other in an equal ratio and in the ratio of 1:1:1:1000 and screened using the gates "High", "Medium", "Low" (FIG. 16), corresponding to the high, medium and low fluorescence of the product. For the 1:1:1:1 ratio, we observed a specific enrichment of each of the BChE mutants with an efficiency close to the theoretical maximum (FIG. 17A, C). Simultaneously, in the case of a 1:1:1:1000 ratio, the enrichment of cl 3 and cl 8 also occurred with an efficiency close to the maximum, while the cl 13 enrichment efficiency was lower for an order of magnitude (FIG. 17B, D).

Thus, if the concentration of cells with activity 2 times higher than background represent a population of more than 0.1%, they can be selected in a single round of screening. At the same time, in the case of cells displaying 5 times higher activity than the control, the efficient selection in single round of screening is possible even for the population which is less than 0.1%. However, the proportion of active cells may be less than 0.001% in the case of highly active wild type DNase, EK and BChE enzymes. The selection of droplets with medium and low fluorescence leads to the efficient elimination of highly active cl 3. This strategy can by used to ultrahigh-throughput identification of mutations leading to the loss of activity of enzymes.

The Creation of New Biocatalysts with a Predesigned Activity Using Ultrahigh-Throughput Screening. Paraoxon (POX)

The BChE library previously described was used for the ultrahigh-throughput selection of BChE mutants, resistant to organophosphates (OP). Yeast cells with anchored BChE mutants were incubated with OP paraoxon (POX) or soman coumarin analogue (GD$_C$), washed out from the excess of OP and screened for the residual BChE activity.

After the single round of screening, two mutants that showed resistance to POX inhibition (cl 14 and cl 15), and six mutants (5 copies of cl 19 mutant and one cl 14) with increased GD$_C$ resistance were selected. These mutants were sequenced and produced in mammalian cell line FreeStyle™ 293-F for kinetic studies to determine the reason of the resistance observed. The interaction between wild type BChE and OP (FIG. 18) leads to the fast (with a high bimolecular rate constant) and irreversible (k2~0) inactivation of BChE resulted from phosphorylation of S198 in the active center.

Unlike wild-type BChE (WT), cl 14 and cl 15 exhibited residual BChE activity even after prolonged inhibition by POX (FIG. 19A). Moreover, in contrast to WT, cl 14 and cl 15 showed catalytic hydrolysis of OP, which was identified using the fluorescent POX-R analog (FIG. 19B). After a rapid covalent modification of cl 14 and WT, leading to the release of a stoichiometric amount of resorufin, WT remains completely modified while cl 14 continues to react slowly with new POX-R molecules, which ultimately results in complete hydrolysis of POX-R.

Thus, the mutants cl 14 and cl 15 display a new paraoxonase activity mediated by self-reactivation ($k_2>0$). Mutant cl 14 had a high reactivity toward POX comparable with WT. Mutant cl 15 also demonstrated the catalytic hydrolysis of POX-R. While, in contrast to cl 14, cl 15 had a significantly lower reactivity toward POX (Table 1).

ganisms in droplets, a simple model system was developed that simulates the interactions between three different types of cells that played the role of "target", "killer" and "mate" (FIG. 20A). The developed scheme was used for the selection of bacteria producing antibiotics that inhibited the growth of pathogenic bacteria *Staphylococcus aureus*. The *S. aureus* strain, constitutively producing a green fluorescent reporter protein (GFP), was used as a "target". Bacteria *Streptomyces venezuelae*, producing the antibiotic chloramphenicol and inhibiting the growth of *S. aureus*, were used as a "killer". *S. venezuelae* produced a wide range of secondary metabolites, including prodignins with red fluorescence, which were used to identify their presence in the drops. *E. coli* cells were used as a neutral "mate" who did not inhibit the growth of *S. aureus*. *E. coli* cells produced the far-red fluorescent reporter protein Katushka2S.

Thus, if *S. aureus* and *S. venezuelae* cells were coencapsulated in one droplet, *S. venezuelae* inhibited the growth of *S. aureus* and filled the entire volume of the droplet, leading to the formation of a droplet with a high level of red and a low level of green fluorescence. In the case that only *S. aureus* cells were encapsulated in the droplet, they were divided uncontrollably leading to the formation of a droplet with intense green fluorescence. If *S. aureus* and *E. coli* cells were coencapsulated in one droplet, both bacteria demonstrated division, which led to the droplet with a high level of green and far-red fluorescence. After cocultivation in droplets, the selection of droplets with the lowest level of green fluorescence led to the enrichment of *S. venezuelae*, but not

TABLE 1

Kinetic constants of wild type BChE (WT) and mutants selected using ultrahigh-throughput screening according to their resistance against POX and $GD_C$.

| OP | POX | | | | $GD_C$ | | | |
|---|---|---|---|---|---|---|---|---|
| | | Selected | | Negative control | | Selected | | Negative control |
| BChE | WT | cl 14 | cl 15 | cl 19 | WT | cl 14 | cl 19 | cl 15 |
| $k_1/K_i \times 10^2$, $M^{-1}s^{-1}$ | 290 ± 30 | 260 ± 40 | 25 ± 4 | 140 ± 20 | 3 ± 1 | 0.5 ± 0.1 | 0.05 ± 0.01 | 2.0 ± 0.5 |
| $k_2 \times 10^4$, $s^{-1}$ | ND | 1.0 ± 0.1 | 1.1 ± 0.1 | ND | ND | ND | ND | ND |

Mutants selected for resistance to $GD_C$ did not display the catalytic hydrolysis of GDC, which was associated with the extremely rapid aging of soman adducts ($t_{1/2}<1$ minute) compared to POX (~8.6 hours) observed for WT BChE. In turn, the increased resistance of the mutant cl 19 selected for the resistance against $GD_C$, was associated with more than 60 fold decrease in reactivity toward $GD_C$.

Thus, in one round of ultrahigh-throughput screening of a relatively small library with representativity of ~$3\times10^5$ enzyme variants, new mutants resistant to OP inhibition were selected. Moreover, in the case of POX, BChE mutants with new artificial catalytic activity were created de novo. As a result, new catalytic antidotes were obtained based on the stoichiometric antidote BChE.

Screening of Antibiotic Activity in Droplets of Microfluidic Double Emulsion

The Model System for Discovery of Pairwise Interactions of Microorganisms.

Biocompatibility is one of the most attractive advantages of the developed platform, which allows the cultivation of microorganisms in droplets of microfluidic double emulsion. To study the pairwise intercellular interactions of microorganisms in droplets,

*E. coli*. The expected results were observed in droplets (FIG. 20B). Every droplet with *S. venezuelae*, obtained after coencapsulation of *S. aureus* and *S. venezuelae* cells in droplets was characterized by intense red fluorescence but not green fluorescence. Most of the droplets that did not have red fluorescence had an intense green fluorescence. On the contrary, in course of coencapsulation of *S. aureus* and *E. coli* cells, the droplets with *E. coli* cells had intense far-red and green fluorescence simultaneously. Subsequent ultrahigh-throughput screening of droplets with the lowest level of green fluorescence using FACS led to the enrichment of *S. venezuelae*, but not *E. coli*, which was identified by cultivation of droplets before and after selection on plates (FIG. 21).

The selection of biocatalysts was carried out on the principle of positive selection, i.e. selection of droplets with the highest level of fluorescence. However, unlike the positive selection, the negative selection of the least fluorescent droplets resulted in a significantly lower degree of enrichment (FIG. 22A). In the case of positive selection, an effective selection of active cells was observed even with their population of about 0.001%. In the case of negative selection, enrichment of killers, but not mates was observed. At the same time, the selection of killers with an efficiency close to the theoretical maximum occurred only if their population was more than 10%. If the proportion of S. venezuelae was less than 1%, the enrichment efficiency decreased.

Figure 22:
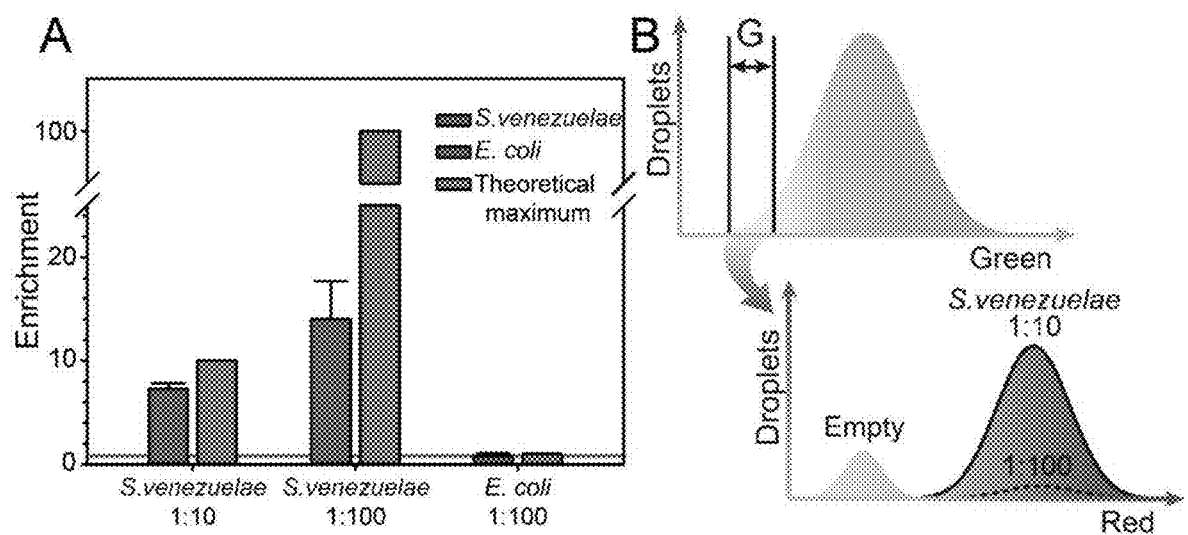
FIG. 22. (A) The enrichment of *S. venezuelae* killers depends on its population. The data presented for a 10 and 1% population of *S. venezuelae*, as well as 1% for *E. coli* cells. (B) The selection of droplets with the lowest level of green fluorescence results in the selection of droplets with encapsulated *S. venezuelae* and empty droplets, which reduce the efficiency of selection.
Figure 23:
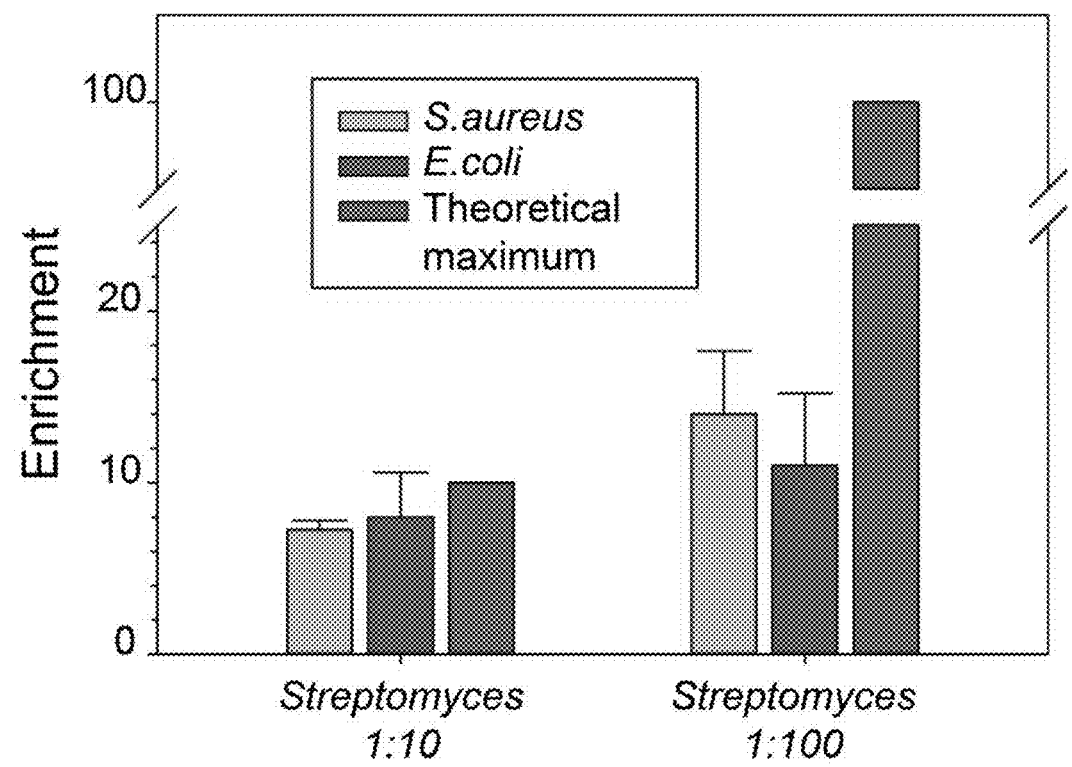
FIG. 23. The enrichment of *S. venezuelae* killers representing the population of 10 and 1% with *S. aureus* and *E. coli* as the target cells.

The observed decrease in the efficiency of selection was associated with the presence of a population of empty droplets, as well as drops in which S. aureus division did not occur due to their transition to persisters or death (FIG. 22B). In order to demonstrate that the utility of this platform is not limited to S. aureus cells as a target, E. coli cells were used. It was also shown that in the case of E. coli cells, inhibited by S. venezuelae, the negative selection leads to low enrichment efficiency of S. venezuelae, if their population is less than 1% (FIG. 23). The results suggest that to provide highly efficient screening based on negative selection of the effector cells representing a population of less than 1%, additional fluorescent reporters based on positive selection are necessary.

Figure 24:
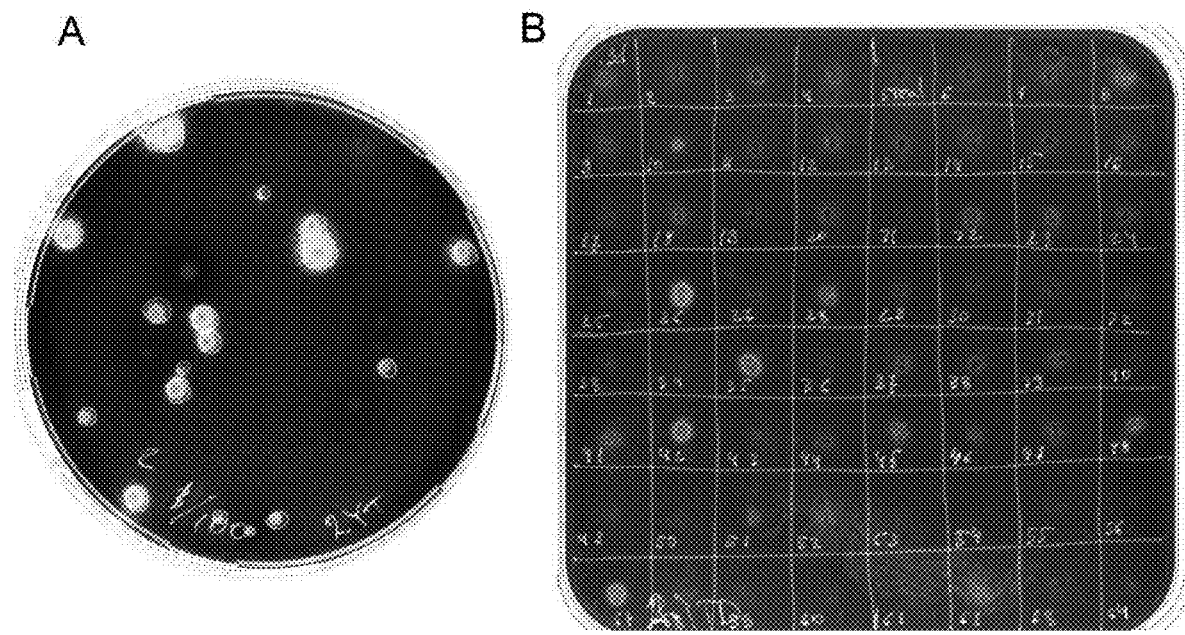
FIG. 24. Identification of bacteria that inhibit the growth of *S. aureus* in the oral microbiota. (A) Formation of clearance zones on the plates with individual colonies of the oral microbiota species, overlayed with *S. aureus* agar. (B) Selection of the most effective inhibitors using plates.

Screening of the Oral Microbiota for Selection of Bacteria Inhibiting the Growth of S. aureus Despite its extremely high pathogenicity, S. aureus is rarely associated with dentoalveolar infections. Hence, there are some unknown natural effectors of the oral microbiota that inhibit the growth of S. aureus. The use of classical bacteriological screening approaches, based on plates (the so-called Waxman platform) showed the presence of bacteria that inhibit the growth of S. aureus in the oral cavity (FIG. 24A). The selected inhibitors showed different sizes of clearance zones (FIG. 24B). Clones with the clearest areas of the largest diameter were used for further work.

Figure 25:
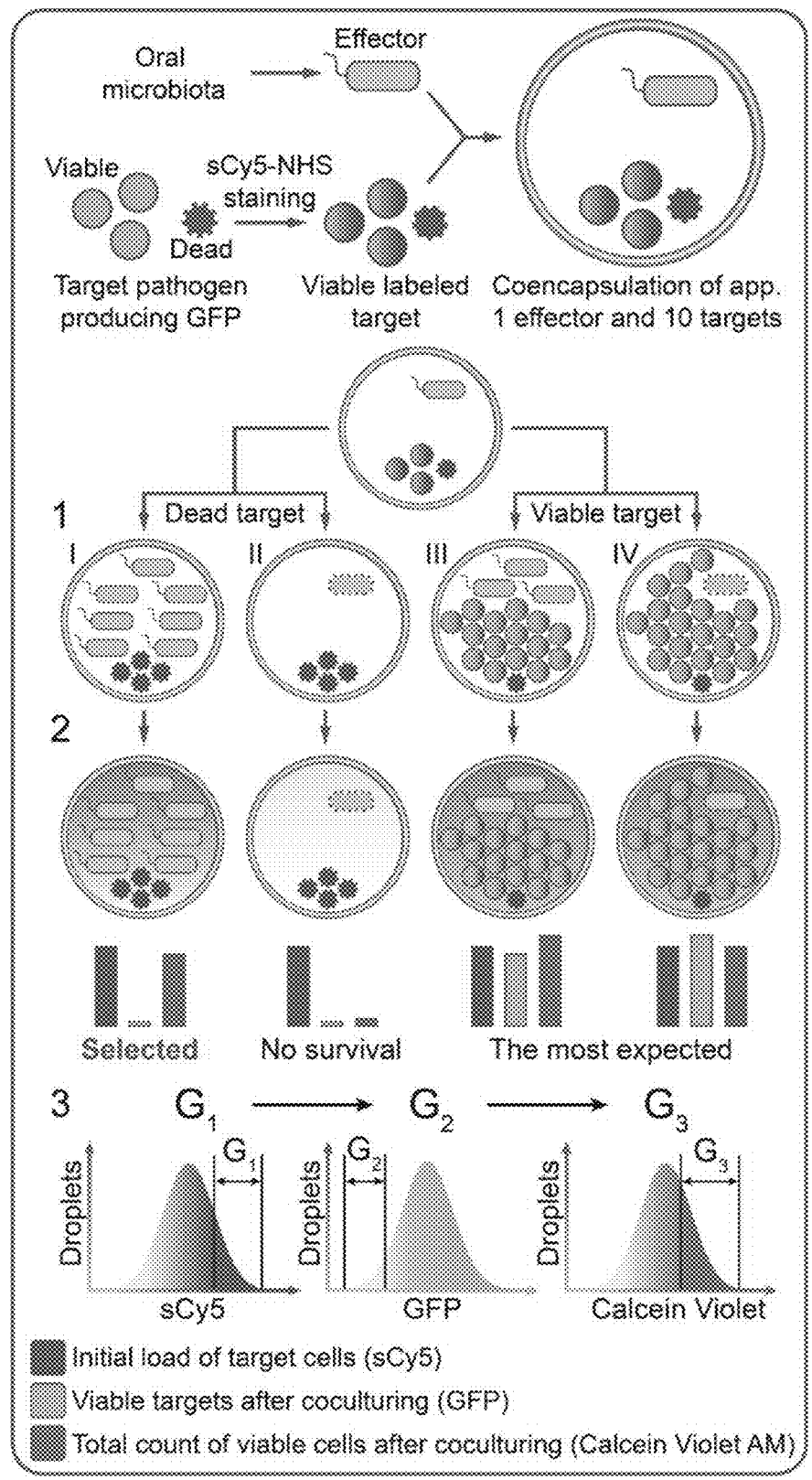
FIG. 25. An improved scheme for the selection of bacteria that inhibit the growth of *S. aureus* using the oral microbiota as a source of biodiversity.

In contrast to the classical Waxman platform, the developed microfluidic platform allows screening of considerably higher biological diversity, which was used to select the bacteria that inhibit the growth of S. aureus among the representatives of the oral microbiota species. For this, the screening scheme developed previously for pairwise interactions in droplets was modified by two additional fluorescent reporter signals to avoid the problem associated with the selection of empty drops and droplets with a low number of encapsulated S. aureus cells (FIG. 25).

The cells of oral microbiota were coencapsulated together with an excess of S. aureus cells labeled with a red fluorescent dye sulfocyanin 5 (sCy5) in droplets of microfluidic double emulsion. The cocultivation of S. aureus and microbiota effectors resulted in four different variants I-IV. I—effector inhibited the growth of S. aureus and remained alive in the process of cocultivation. II—effector and S. aureus died. III—effector and S. aureus were cocultivated in a droplet and did not inhibit the growth of each other. IV—S. aureus inhibited the growth of the effector. In order to distinguish between these variants, Calcein Violet AM, a non-fluorescent, hydrophobic acetoxymethyl ester capable of penetrating through a layer of oil phase, was used.

If the living cells are present in a droplet, their esterases hydrolyze acetoxymethyl ether, which in turn leads to the formation of a highly hydrophilic product with intense blue fluorescence, incapable of transport through the hydrophobic oil layer. Thus, the selection of a population of droplets with a high level of red, low green and high blue fluorescence leads to the selection of droplets with a high initial load of S. aureus cells that did not proliferate in droplets, while living cells other than S. aureus were present in the droplets.

Figure 26:
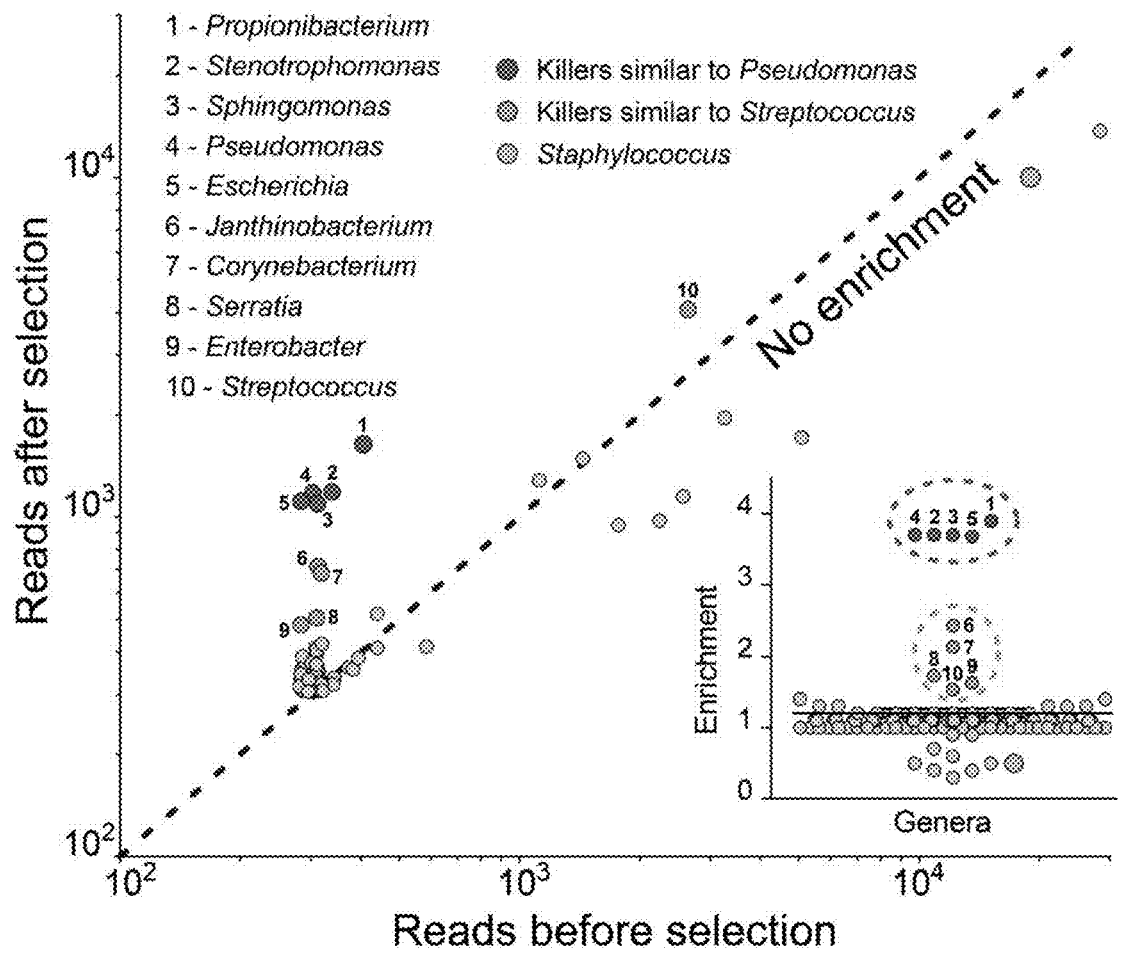
FIG. 26. Prediction of bacterial genera that inhibit the growth of *S. aureus*, according to the results of 16S rRNA sequencing.

Since different bacteria have different growth rates and can inhibit the growth of each other on the plates, the selected drops were subjected to direct 16S rRNA and whole genome (WGS) high-throughput sequencing in order to identify slow-growing and unculturable bacteria that inhibit S. aureus growth in the droplets. The comparison of the number of readings before and after selection showed that, according both to the results of 16S rRNA sequencing (FIG. 26) and WGS, Propionibacterium acnes was the most enriched bacteria.

16S rRNA sequencing revealed two subpopulations of bacterial inhibitors selected with different efficacy. Bacteria that belong to the genera Propionibacterium, Stenotrophomonas, Sphingomonas, Pseudomonas, and Escherichia had the highest level of enrichment, while Corynebacterium, Janthinobacterium, Serratia, Enterobacter and Staphylococcus were also significantly enriched. Staphylococcus was the most common inhibitor of S. aureus among the oral microbiota. WGS confirmed the extremely efficient enrichment of slow-growing Propionibacterium acnes, also allowing the identification of inhibitor bacteria species. The Staphylococcus mitis group (S. pneumoniae, S. mitis, S. oralis and S. pseudopneumoniae), Prevotella dentalis (slow-growing), Staphylococcus epidermidis (well-known S. aureus effector) and Pseudomonas aeruginosa were significantly enriched after the selection with ultrahigh-throughput screening in droplets.

Figure 27:
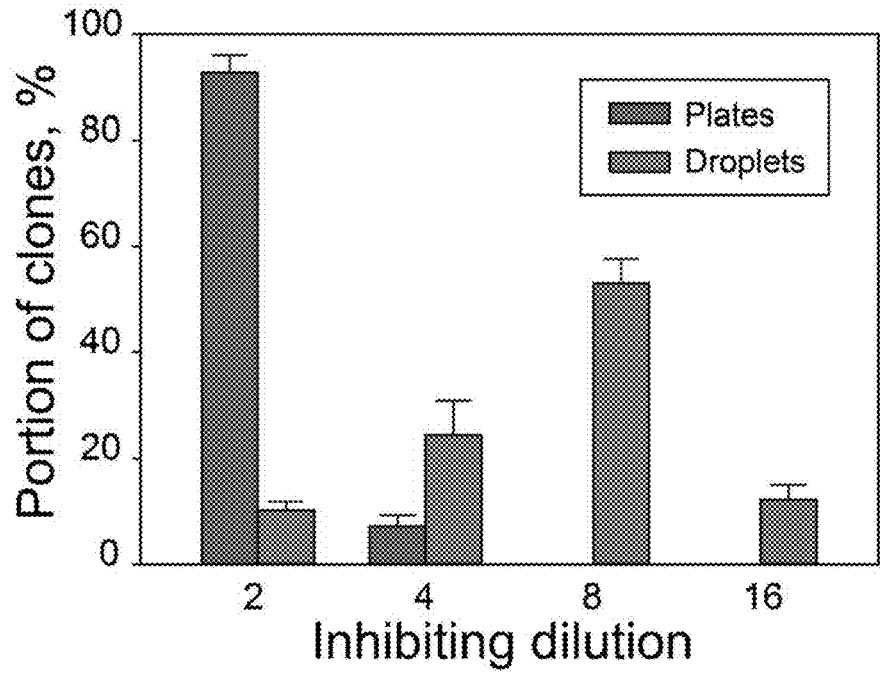
FIG. 27. Streptococcal clones selected using a microfluidic platform (droplets) showed significantly more efficient inhibition of *S. aureus* growth than clones obtained using conventional Waxman platform (plates).

The selected droplets were also cultivated to identify culturable S. aureus inhibitors. More than 90% of bacterial colonies, other than S. aureus, regenerated from droplets on the plates, belonged to the genus Staphylococcus. More than 64% of them were classified by mass spectrometry as Staphylococcus oralis. Selected clones produced metabolites that inhibit the growth of S. aureus. Staphylococcus oralis showed the greatest inhibitory dilution of the growth medium (up to 16 fold dilution). The clones obtained by selection with ultrahigh-throughput screening in droplets had a significantly higher inhibitory dilution of the growth medium than clones obtained using classical plate screening (FIG. 27).

Cocultivation of diluted ($<10^6$ CFU/ml) culture of Staphylococcus oralis and S. aureus, however, did not lead to inhibition of S. aureus growth, which, apparently, is associated with a much faster kinetics of S. aureus growth. At the same time, the physiological significance of Staphylococcus oralis can be very high. The real conditions differ significantly from what was observed during cocultivation, since saliva is a much poorer growth medium, and local concentrations of streptococci on the gum surface are much higher, than those that were used in liquid culture. In addition, effective inhibition of S. aureus was observed on plates, which also suggests that streptococci, in particular Staphylococcus oralis, can play an important physiological role as a protective barrier preventing the colonization of S. aureus.

Figure 28:
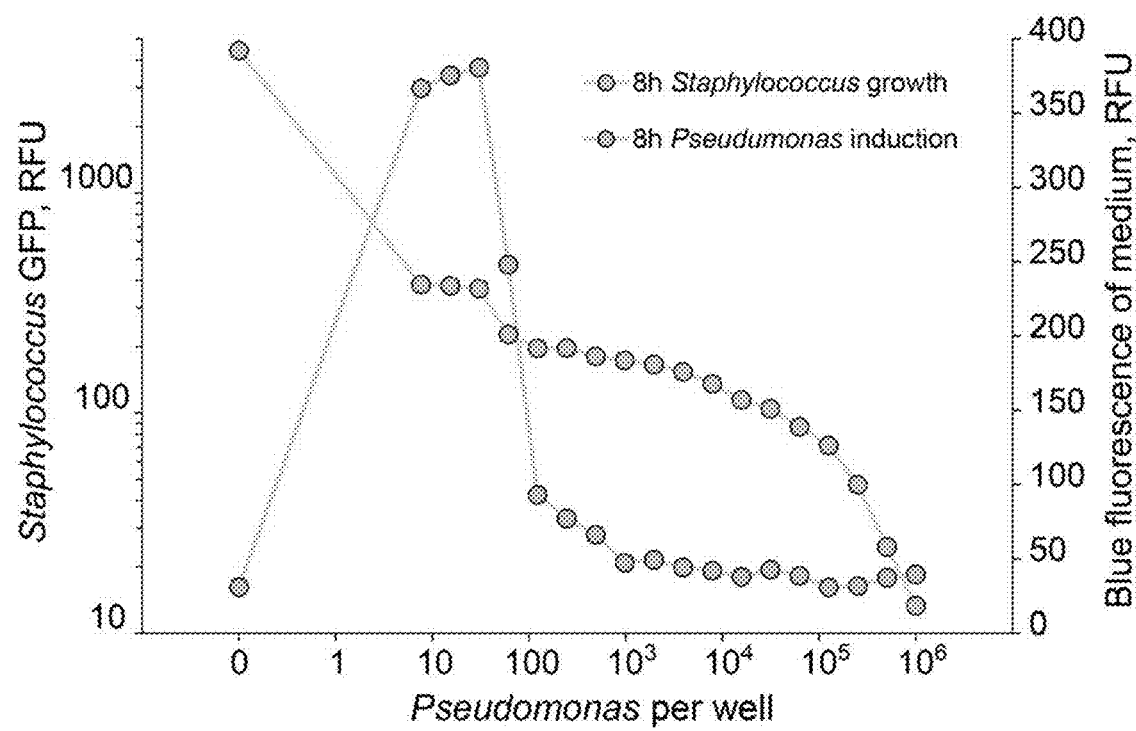
FIG. 28. *P. aeruginosa* inhibited the growth of *S. aureus* in coculture even at single cell level.

The Pseudomonas aeruginosa strain was selected exclusively using the microfluidic platform, completely inhibiting the growth of S. aureus in culture even on a single cell level (FIG. 28). Opportunistic pathogen P. aeruginosa is not a normal component of the oral microflora. It was present in oral microbiota in an extremely low concentration of <0.005%. This made its selection impossible using the classical Waxman platform. S. oralis, unlike P. aeruginosa, produced secondary metabolites that inhibit the growth of S. aureus inducibly in the process of cocultivation with S. aureus. The maximum level of induction corresponded to the minimum concentration of P. aeruginosa in the growth medium during cocultivation (FIG. 28) and correlated with blue fluorescence of pyoverdine. However, the growth inhibition of S. aureus was not mediated by pyoverdine.

Figure 29:
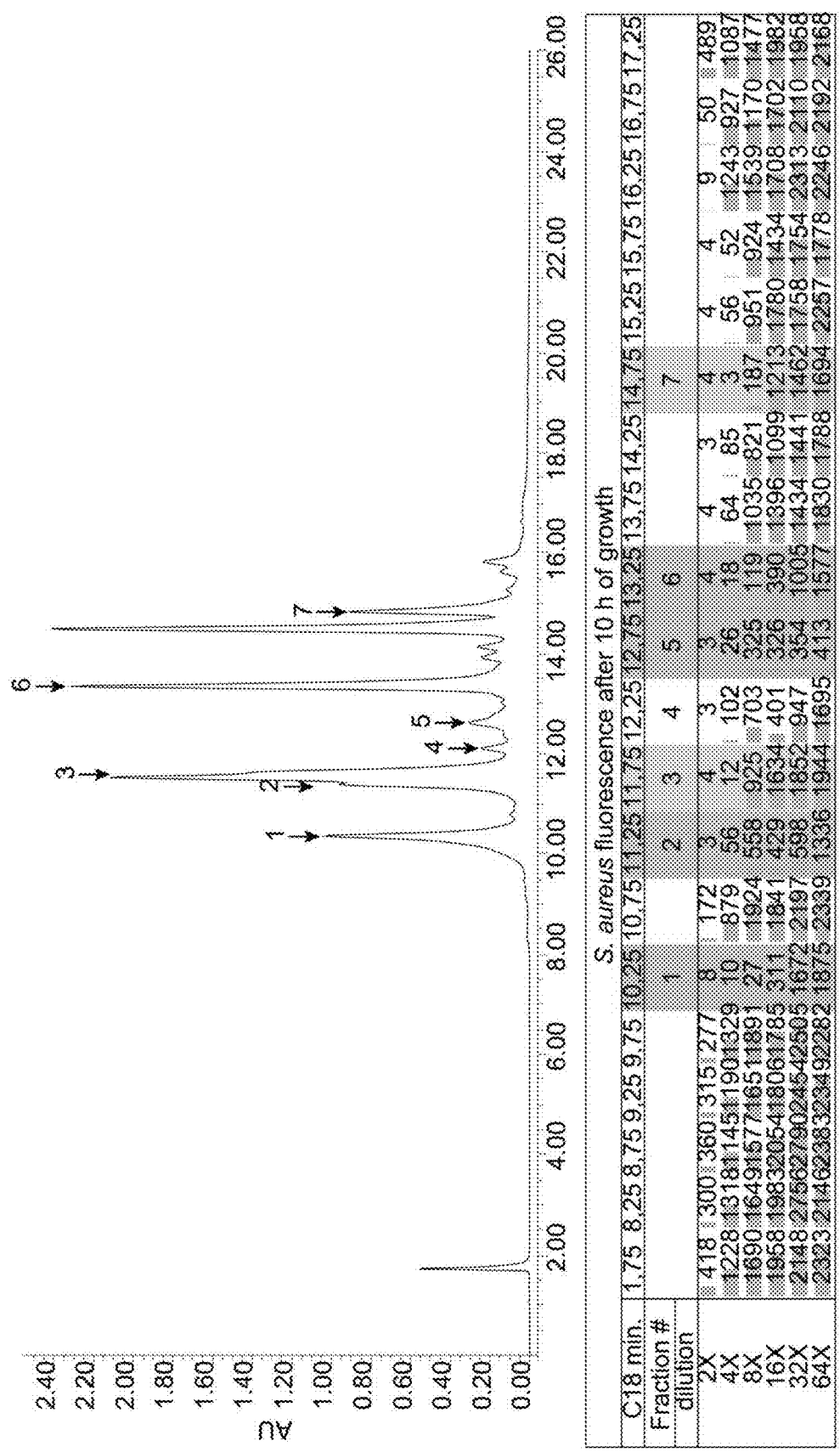
FIG. 29. Fractionation of chloroform extract of *P. aeruginosa* culture medium and the analysis of the inhibitory activity of the obtained fractions.

The chloroform extract of *P. aeruginosa* growth medium obtained after cocultivation of an excess of *S. aureus* over *P. aeruginosa*, was fractionated using reverse phase HPLC (FIG. 29). *P. aeruginosa* produced a wide range of secondary metabolites that inhibited the growth of *S. aureus*.

Figure 30:
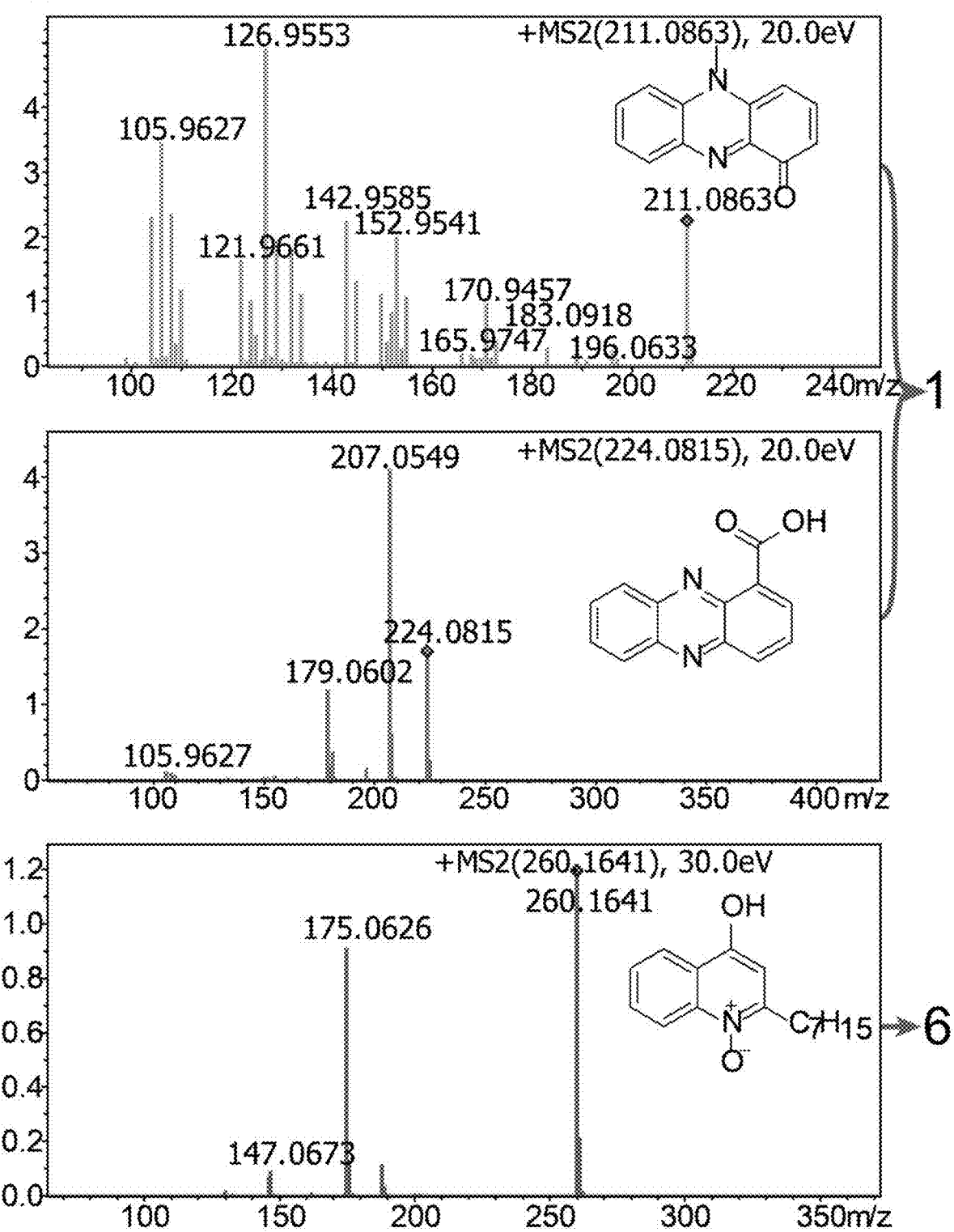
FIG. 30. (A) Synergistic inhibition of *S. aureus* growth by fractions 1 and 6, obtained by fractionation using HPLC. (B) Basic active compounds of fractions 1 and 6, identified using mass spectrometry.

Fractions 1 and 6 demonstrated highly efficient synergistic inhibition, leading to the death of *S. aureus* (FIG. 30A). The main active substances identified by mass spectrometry (FIG. 30B) were pyocyanin and phenazin-1-carboxylic acid (fraction 1) and 2-heptyl-4-hydroxyquinoline N-oxide (fraction 6). Pyocyanin and phenazin-1-carboxylic acid are catalase inhibitors, also acting as electron transport chain carriers, mediating the production of reactive oxygen species. While 2-heptyl-4-hydroxyquinoline N-oxide inhibits the oxidation pathway of hydroquinones. Thus, *P. aeruginosa* controls the growth of *S. aureus* using synergistic mechanisms that target the induction of oxidative stress and leading to the *S. aureus* death.

The invention claimed is:

1. A method for ultrahigh-throughput screening of a mixture of cells to isolate cells having an antimicrobial activity, the method comprising: generating a double microfluidic water-in-oil-in-water (W/O/W) emulsion comprising monodisperse droplets encapsulating individual cells or mixture of cells in individual droplet microcompartments, which monodisperse droplets have controlled diameters ranging from 20 to 90 μm, wherein said double water-in-oil-in-water (W/O/W) emulsion is generated by sequential microfluidic emulsification of a water phase comprising mixed streams of cells in the mixture of cells and an indicator that changes in fluorescence when activated by cells in the mixture of cells that have antimicrobial activity, wherein the indicator comprises target cells that change in fluorescence when inhibited or killed by the antimicrobial activity of cells in the mixture, and an oil phase to produce a water-in-oil emulsion, followed by microfluidic emulsification of water-in-oil emulsion in outer aqueous phase to produce monodisperse double water-in-oil-in-water (W/O/W) emulsion; isolating a population of monodisperse droplets containing cells having the antimicrobial activity by an ultrahigh-throughput method comprising fluorescence-activated cell sorting (FACS); optionally regenerating or culturing cells from isolated droplets; analyzing the genome or metabolism of the isolated cells having the specific antimicrobial activity; with or without regenerating or culturing— the isolated cells.

2. The method of claim 1, wherein the mixture of cells comprises microbiota.

3. The method of claim 1, wherein the mixture of cells comprises cells exhibiting different types or different levels of enzymatic or biocatalytic activities.

4. The method of claim 1, wherein the mixture of cells comprises a library of cellular phenotypes.

5. The method of claim 1, wherein generating a double water-in-oil-in-water (W/O/W) emulsion comprises monodisperse droplets encapsulating individual living cells, dividing living cells, or a mixture of cells in individual droplet microcompartments, wherein said living or living dividing cells comprise analyzed, isolated or regenerated cells.

6. The method of claim 1, wherein the indicator comprises target cells that are *Streptococcus aureus* cells.

7. The method of claim 1, wherein the mixture of cells comprises a library of cellular phenotypes having new artificial activities.

8. The method of claim 7, wherein the mixture of cells comprise oral microbiota; wherein the indicator is combination of a fluorogenic/fluorescent compound and a reporter target cell that changes in fluorescence when growth of the target cell is inhibited; and wherein the ultrahigh-throughput method comprises isolating droplets whose combination of fluorescence signals has changed indicating that target cell growth has been inhibited.

9. The method of claim 8, wherein the target cell produces green fluorescent protein (GFP) and its green fluorescence decreases after its growth is inhibited; wherein said ultrahigh-throughput method separates a subpopulation of cells having decreased or no green fluorescence; and wherein said subpopulation of cells have their 16S rRNA or whole genomes sequenced and/or are cultivated, fractionated, and have their components analyzed.

10. The method of claim 9, wherein the subpopulation of cells is cultured, metabolites are fractionated by reverse phase HPLC, and the anti-target cell activity of the fractions determined, and, optionally, have active fractions analyzed by mass spectrometry and have active metabolites identified.

11. The method of claim 1, wherein the indicator comprises a fluorogenic/fluorescent compound changing its fluorescence (level or spectrum) by interacting with the cells having a specific enzymatic or biocatalytic activity.

12. The method of claim 1, wherein the indicator comprises a reporter target cell, wherein fluorescence of the reporter target cell changes when it interacts with the cells having the antimicrobial activity.

13. The method of claim 1, wherein a combination of different fluorescent indicators probes is used for isolation of cells with the antimicrobial activity.

14. The method of claim 1, wherein the antimicrobial activity inhibits the growth of the target s cells.

15. The method of claim 1, wherein the antimicrobial activity kills the target cells.

16. The method of claim 1, wherein the water-in-oil emulsion is generated in a first hydrophobic chip and the resulting single oil-in-water emulsion is reemulsified in external aqueous phase in a second hydrophilic chip to generate the double water-in-oil-in-water emulsion.

17. The method of claim 16, wherein the chips have channels that range in diameter from 20 to 60 μm that generate a monodisperse double microfluidic emulsion having droplets with a controlled diameter ranging from 20 to 90 μm.

18. The method of claim 16, wherein the first hydrophobic chip has been made hydrophobic by treatment with a hydrophobizer that is trichloroctadecylsilane or AQUAPEL®.

19. The method of claim 1, wherein the surface of the second chip has been made hydrophilic by treatment with polyvinylalcohol.

20. The method of claim 1, wherein the ultrahigh-throughput method has a productivity of 1000-20000 events per second.

\* \* \* \* \*

SEQUENCE LISTING

```
<160> NUMBER OF SEQ ID NOS: 1

<210> SEQ ID NO 1
<211> LENGTH: 31
<212> TYPE: DNA
<213> ORGANISM: Artificial Sequence
<220> FEATURE:
<223> OTHER INFORMATION: DNase substrate

<400> SEQUENCE: 1
aaaaaaaccc ccccatatag cgcgtttttt t                              31
```